US005474705A

United States Patent [19]

Janulis et al.

[11] Patent Number: 5,474,705
[45] Date of Patent: Dec. 12, 1995

[54] CHIRAL LIQUID CRYSTAL COMPOUNDS HAVING A PERFLUOROETHER TERMINAL PORTION

[75] Inventors: Eugene P. Janulis, Mahtomedi; Gilbert C. Johnson, Lino Lake; Marc D. Radcliffe, Woodbury; Patricia M. Savu, Maplewood; Daniel C. Snustad, Woodbury; Terence D. Spawn, West Lakeland Township, Washington County, all of Minn.

[73] Assignee: Minnesota Mining and Manufacturing Company, St. Paul, Minn.

[21] Appl. No.: 338,961

[22] Filed: Nov. 14, 1994

Related U.S. Application Data

[63] Continuation-in-part of Ser. No. 171,569, Dec. 22, 1993, abandoned.

[51] Int. Cl.$^6$ .......................... C09K 19/52; C09K 19/30; C09K 19/32; G02F 1/13

[52] U.S. Cl. .................. 252/299.01; 252/299.61; 252/299.62; 252/299.63; 252/299.64; 252/299.65; 252/299.66; 252/299.67; 544/298; 544/335; 546/270; 546/315; 546/322; 546/326; 549/369; 549/374; 549/271; 549/266; 549/267; 560/64; 560/65; 359/103

[58] Field of Search .................. 252/299.01, 299.61, 252/299.62, 299.63, 299.64, 299.65, 299.66, 299.67; 544/298, 335; 546/270, 315, 322, 326; 549/369, 374, 180; 560/64, 65; 568/325, 331, 642; 570/129; 359/103

[56] References Cited

U.S. PATENT DOCUMENTS

5,141,669   8/1992   Bloom et al. .................. 252/299.65

FOREIGN PATENT DOCUMENTS

255236      2/1988    European Pat. Off. ........ C09K 19/20
WO93/22396  11/1993   WIPO .......................... C09K 19/34

OTHER PUBLICATIONS

H. Nohira et al., Mol. Cryst. Liq. Cryst. 180B, 379–88 (1990).

P. M. Savu, *Kirk–Othmer Encyclopedia of Chemical Technology*, Fourth Edition, vol. 11, pp. 558–564, John Wiley & Sons, New York (1994).

Patent Abstracts of Japan, vol. 15, No. 271 (C–0848), Jul. 10. 1991.

*Primary Examiner*—Shean Wu
*Attorney, Agent, or Firm*—Gary L. Griswold; Walter N. Kirn; Lucy C. Weiss

[57] ABSTRACT

Fluorine-containing, chiral liquid crystal compounds comprise (a) an aliphatic fluorocarbon terminal portion containing at least two catenary ether oxygen atoms; (b) a chiral, aliphatic hydrocarbon terminal portion; and (c) a central core connecting the terminal portions. The compounds have smectic mesophases or latent smectic mesophases and are useful, for example, in liquid crystal display devices.

21 Claims, No Drawings

CHIRAL LIQUID CRYSTAL COMPOUNDS HAVING A PERFLUOROETHER TERMINAL PORTION

This application is a continuation-in-part of application Ser. No. 08/171,569 filed Dec. 22, 1993. now abandoned.

FIELD OF THE INVENTION

This invention relates to fluorinated chiral smectic liquid crystal compounds, to a process for the preparation of such compounds, and to liquid crystal compound mixtures and electrooptical display devices containing such compounds.

BACKGROUND OF THE INVENTION

Devices employing liquid crystals have found use in a variety of electrooptical applications, in particular those which require compact, energy-efficient, voltage-controlled light valves, e.g., watch and calculator displays, as well as the flat-panel displays found in portable computers and compact televisions. Liquid crystal displays have a number of unique characteristics, including low voltage and low power of operation, which make them the most promising of the non-emissive electrooptical display candidates currently available. However, slow response and insufficient nonlinearity can impose limitations for many potential applications. The requirement for speed may become especially important in proportion to the number of elements which have to be addressed in a device. This limits the potential use of some types of liquid crystals.

The modes of liquid crystal displays that are most extensively employed at the present are twisted nematic (TN), supertwisted birefringence effect (SBE), and dynamic scattering (DS), all employing nematic or chiral nematic (cholesteric) liquid crystals. These devices are based upon the dielectric alignment effects (Freedericksz effect) of the nematic and/or chiral nematic liquid crystal (or mixtures of nematic or chiral nematic liquid crystals) upon application of an electric field. The average molecular long axis of the liquid crystal material takes up a preferred orientation in the applied electric field, the orientation of which is dependent on the sign of the dielectric anisotropy of the material or mixture, and this orientation relaxes upon removal of the applied electric field. This reorientation and relaxation is slow, on the order of a few milliseconds.

Although nematic and chiral nematic liquid crystals are the most extensively employed, there are liquid crystal devices that employ more highly ordered smectic liquid crystals. For example, materials with a smectic A mesophase are useful in device applications, as described by Crossland et al. in U.S. Pat. Nos. 4,411,494, 4,419,664, and 4,528,562, and by F. J. Kahn in Appl. Phys. Lett. 22, 111 (1973). These devices are based on the dielectric reorientation of the liquid crystals, and response times are on the order of milliseconds.

Mixtures which exhibit a chiral smectic A mesophase are also useful in device applications, as described by Lagerwall et al., 1st International Symposium On Ferroelectric Liquid Crystals, Bordeaux-Arcachon, France, 1987. These mixtures exhibit an electrooptic effect which is termed a soft-mode ferroelectric effect, and sub-microsecond switching can be achieved.

Materials with a smectic C mesophase are useful in device applications, as described by Pelzl et al. in Kristall Technik. 14, 817 (1979), Mol. Cryst. Liq. Cryst. 53, 167 (1979), and Liquid Crystals 2, 21, 131 (1987). These devices are based on the dielectric reorientation of the liquid crystals, and the response times are slow.

A recent advance in the liquid crystal art has been the utilization of tilted chiral smectic liquid crystals, which are also termed ferroelectric liquid crystals, in devices which give microsecond switching and bistable operation not possible in any of the device applications described above. Ferroelectric liquid crystals were discovered by R. B. Meyer et al. (J. Physique 36, 1–69 (1975)). A high speed optical switching phenomenon was discovered for the ferroelectric liquid crystals by N. A. Clark et al. (Appl. Phys. Lett. 36, 899 (1980) and U.S. Pat. No. 4,367,924).

Fluorine-containing ferroelectric liquid crystal materials have recently been developed. U.S. Pat. No. 4,886,619 (Janulis) discloses fluorine-containing, chiral smectic liquid crystal compounds which comprise a fluorocarbon terminal portion and a chiral hydrocarbon terminal portion, the terminal portions being connected by a central core. U.S. Pat. No. 5,082,587 (Janulis) discloses achiral, fluorine-containing liquid crystal compounds which comprise a fluorocarbon terminal portion and a hydrocarbon or another fluorocarbon terminal portion, the terminal portions being connected by a central core. U.S. Pat. No. 5,262,082 (Janulis et al.) describes achiral, fluorine-containing liquid crystal compounds comprising an aliphatic fluorocarbon terminal portion having at least one catenary ether oxygen and an aliphatic hydrocarbon terminal portion, the terminal portions being connected by a central core.

International Publication Nos. WO 88/03530 (Merck) and WO 91/00897 (Merck) disclose chiral or achiral ring compounds which may be used as components of chiral, tilted, smectic liquid-crystalline phases with ferroelectric properties.

U.S. Pat. No. 5,051,527 (Suzuki et al.) describes novel ferroelectric liquid crystal compounds having an optically active fluoroalkyl radical.

The high speed switching of the ferroelectric liquid crystals can be utilized in many applications, e.g., light valves, displays, printer heads, and the like. In addition to the microsecond switching speeds, some ferroelectric liquid crystal device geometries exhibit bistable, threshold-sensitive switching, making them candidates for matrix-addressed devices containing a large number of elements for passive displays of graphic and pictorial information, as well as optical processing applications.

SUMMARY OF THE INVENTION

Briefly, in one aspect, this invention provides fluorine-containing, chiral liquid crystal compounds having smectic mesophases or latent smectic mesophases. (Compounds having latent smectic mesophases are those which by themselves do not exhibit a smectic mesophase, but which, when in admixture with compounds having smectic mesophases or with other compounds having latent smectic mesophases, develop smectic mesophases under appropriate conditions.) The chiral liquid crystal compounds of the invention comprise (a) an aliphatic fluorocarbon terminal portion containing at least two catenary, i.e., in-chain, ether oxygen atoms; (b) a chiral, aliphatic hydrocarbon terminal portion; and (c) a central core connecting the terminal portions. The aliphatic fluorocarbon terminal portion can be represented by the formula $-D(C_xF_{2x}O)_zC_yF_{2y+1}$, where x is independently an integer of 1 to about 10 for each $C_xF_{2x}O$ group, y is an integer of 1 to about 10, z is an integer of 2 to about 10, and D is selected from the group consisting of a covalent bond,

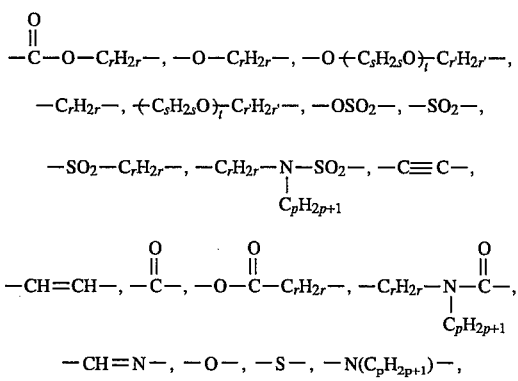

$-CH=N-$, $-O-$, $-S-$, $-N(C_pH_{2p+1})-$, and combinations thereof, where r and r' are independently integers of 1 to about 20, s is independently an integer of 1 to about 10 for each $(C_sH_{2s}O)$, t is an integer of 1 to about 6, and p is an integer of 0 to about 4. The $(C_xF_{2x}O)_zC_yF_{2y+1}$ group of the fluorocarbon terminal portion can contain small amounts of residual carbon-bonded hydrogen atoms but is preferably completely fluorinated. Preferably, the fluorocarbon terminal portion is a linear group represented by the formula $-D(C_xF_{2x}O)_zC_yF_{2y+1}$, where x is independently an integer of 1 to about 6 for each $C_xF_{2x}O$ group, y is an integer of 1 to about 6, and z is an integer of 2 to about 6.

In general, the compounds of this invention have a central core comprised of at least one or two rings independently selected from the group consisting of aromatic, heteroaromatic, alicyclic, substituted aromatic, substituted heteroaromatic, and substituted alicyclic rings, the rings being connected one with another by a covalent bond or by chemical groups selected from the group consisting of —COO—, —COS—, —HC=N—, —CH=CH—, —C≡C—, and —COSe—. The rings can be fused or non-fused. The heteroatoms within the heteroaromatic rings comprise at least one atom selected from the group consisting of nitrogen, oxygen, and sulfur. Non-adjacent methylene groups in the alicyclic rings can be substituted by oxygen or sulfur atoms.

The chiral liquid crystal compounds of the present invention are optically active (except when in the form of a racemic mixture) and are useful alone or in admixture with other chiral or achiral liquid crystal compounds for electrooptical display applications. The compounds of the invention have a number of desirable properties when used in admixture with other liquid crystal compounds, preferably compounds having fluorinated terminal portions such as those compounds disclosed, for example, in U.S. Pat. Nos. 4,886,619 (Janulis), 5,082,587 (Janulis), and 5,262,082 (Janulis et al.). For example, the compounds of the invention when admixed with such preferred liquid crystal compounds show good compatibility, show only a minimal effect on the smectic C temperature range of the resulting mixtures, and provide ferroelectric mixtures which are switchable and bistable.

Most importantly, the chiral, fluorine-containing compounds of the invention when used in admixture with the achiral, fluorine-containing liquid crystal compounds of U.S. Pat. No. 5,262,082 (Janulis et al.) provide mixtures which exhibit higher memory to tilt angle ratios than mixtures of the same achiral compounds with chiral, hydrocarbon liquid crystal compounds. This is important because a high memory to tilt angle ratio is essential for a high contrast ferroelectric liquid crystal device (i.e., the memory to tilt angle ratio should ideally be equal to one in order for a liquid crystal display device to have an optimum contrast ratio).

(See, e.g., the discussion by A. Mochizuki et al., SPIE 1665, 108–09 (1992), as well as European Pat. Publication No. 0 548 548 A1 (Canon Kabushiki Kaisha).)

The fluorine-containing liquid crystal compounds of the invention also have good chemical stability toward water, weak acids, and weak bases; do not undergo degradation during normal use in a liquid crystal display device; and are photochemically stable, i.e., do not easily undergo photochemical reactions. Many of these compounds, due to the aliphatic fluorocarbon terminal portion, have enhanced smectogenic properties and lower birefringences than their non-fluorine-containing analogues. The compounds, and mixtures which contain them, are useful in a variety of electrooptical displays. In particular, many of these fluorinated materials exhibit smectic mesophases and are useful in the formulation of nematic; chiral nematic, i.e., cholesteric; smectic A (SmA); smectic C (SmC); chiral smectic A (SmA*); and chiral smectic C (SmC*) mixtures.

In other aspects, this invention also provides a mixture of liquid crystal compounds comprising at least one liquid crystal compound of the invention, a liquid crystal display device containing at least one liquid crystal compound of the invention, and a process for preparing the liquid crystal compounds of the invention.

DETAILED DESCRIPTION OF THE INVENTION

The liquid crystal compounds of the present invention can be represented by the general formula I:

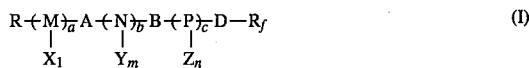

where M, N, and P are each independently selected from the group consisting of

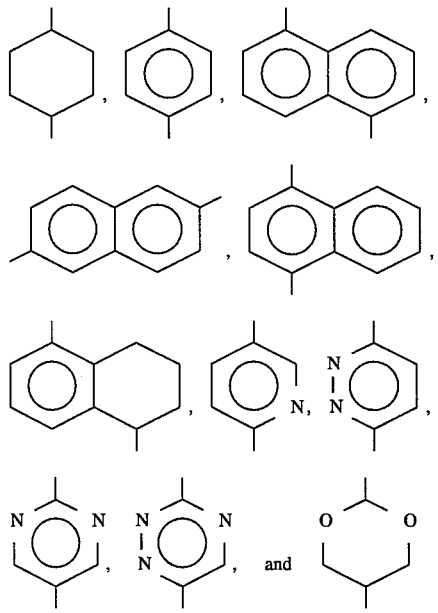

a, b, and c are each independently zero or an integer of from 1 to 3, with the proviso that the sum of a+ b +c be at least 1;

each A and B are non-directionally and independently selected from the group consisting of a covalent bond,

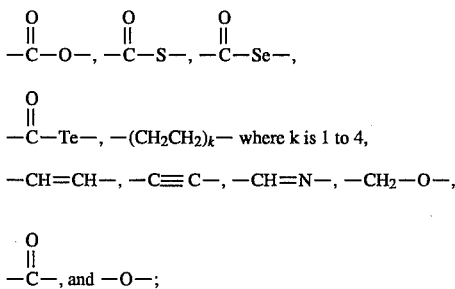

each X, Y, and Z are independently selected from the group consisting of —H, —Cl, —F, —Br, —I, —OH, —OCH$_3$, —CH$_3$, —CF$_3$, —OCF3 —CN, and —NO$_2$;

each l, m, and n are independently zero or an integer of 1 to 4;

D is selected from the group consisting of a covalent bond,

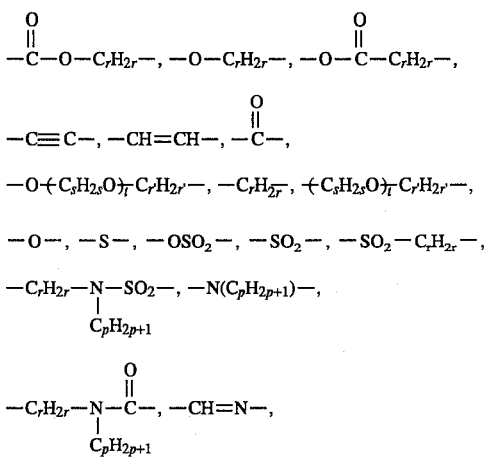

and combinations thereof, where r and r' are independently integers of 1 to about 20, s is independently an integer of 1 to about 10 for each (C$_s$H$_{2s}$O), t is an integer of 1 to about 6, and p is an integer of 0 to about 4;

R is selected from the group consisting of —O—((C$_{q'}$H$_{2q'-v'}$—R'$_{v'}$)—O)$_w$—C$_q$H$_{2q+1-v}$—R'$_v$, —((C$_{q'}$H$_{2q'-v'}$—R'$_{v'}$)—O)$_w$—C$_q$H$_{2q+1-v}$—R'$_v$, T,102 where each R' is independently selected from the group consisting of —Cl, —F, —CF$_3$, —NO$_2$, —CN, —H, —C$_q$H$_{2q+1}$,

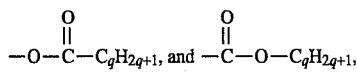

where q' is independently an integer of 1 to about 20 for each (C$_{q'}$H$_{2q'}$—O), q is an integer of 1 to about 20, w is an integer of 0 to about 10, v is an integer of 0 to about 6, each v' is independently an integer of 0 to about 6, g is an integer of 1, g' is an integer of 1, each D is independently selected from the group set forth above other than C≡C, with the proviso that R is chiral; and R$_f$ is —(C$_x$F$_{2x}$O)$_z$C$_y$F$_{2y+1}$, where x is independently an integer of 1 to about 10 for each (C$_x$F$_{2x}$O), y is an integer of 1 to about 10, and z is an integer of 2 to about 10. Preferably, R$_f$ is linear, x is independently an integer of 1 to about 6 for each (C$_x$F$_{2x}$O), y is an integer of 1 to about 6, and z is an integer of 2 to about 6.

Preferred classes of the chiral compounds of the invention can be represented by the following formulas:

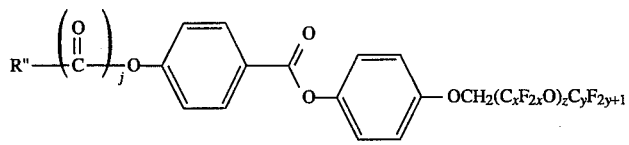

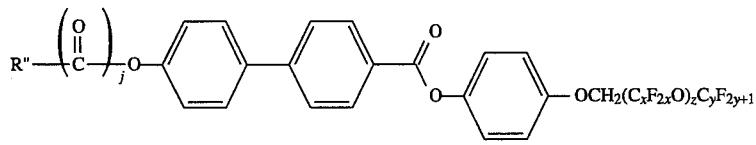

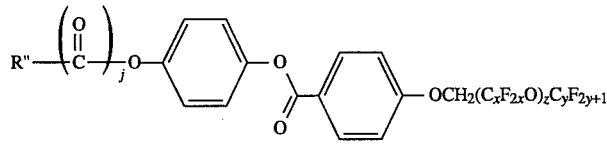

-continued

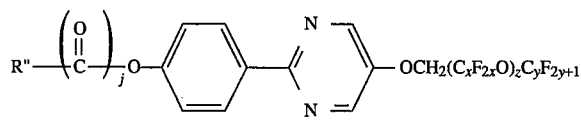

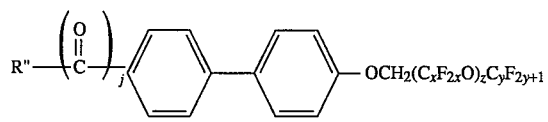

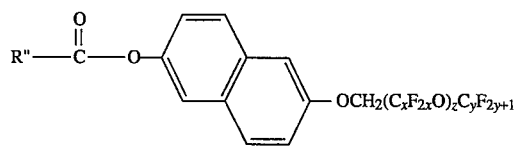

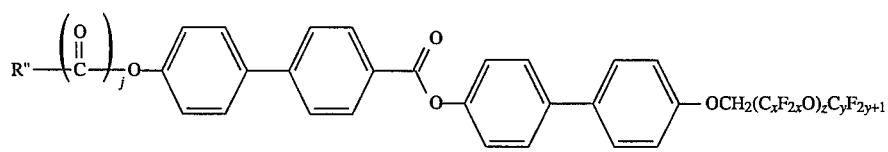

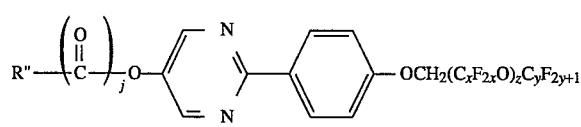

where x is independently an integer of 1 to about 6 for each $C_xF_{2x}O$; y is an integer of 1 to about 6; z is an integer of 2 to about 4; j is an integer of 0 or 1; and R" is selected from the group consisting of $R'_v-C_qH_{2q+1-v}$ and

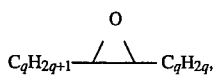

where each q is independently an integer of 2 to about 10; each R' is independently selected from the group consisting of hydrogen, fluorine, chlorine, methyl, and perfluoromethyl; v is an integer of 1 to about 4; and $C_qH_{2q}$ and $C_qH_{2q+1}$ can be linear or branched.

Many of the compounds of the present invention have suppressed nematic mesophases (i.e., exhibit no or very small nematic mesophase temperature ranges) and enhanced smectic mesophases. Mixtures of the compounds of the invention with other liquid crystal materials can be formulated to provide desired transition temperatures and broad mesophase temperature ranges. Such mixtures preferably contain compounds having fluorinated terminal portions, such as those compounds described, for example, in U.S. Pat. Nos. 4,886,619 (Janulis), 5,082,587 (Janulis), and, most preferably, 5,262,082 (Janulis et al.), the descriptions of which are incorporated herein by reference.

The compounds of this invention in admixture with other chiral or achiral liquid crystal compounds exhibit chiral smectic (ferroelectric) liquid crystal behavior. Furthermore, the compounds of the invention when mixed with achiral, fluoroether-containing liquid crystal compounds (e.g., those described in U.S. Pat. No. 5,262,082 (Janulis et al.)) exhibit a reduced temperature dependence of the smectic interlayer spacing. This property provides for the spontaneous generation of a bookshelf layer structure, which is ideal for a ferroelectric liquid crystal device.

Another advantage of using the materials of this invention in the formulation of liquid crystal mixtures is the low birefringence which can be obtained. The low birefringence of the liquid crystal compounds of the invention (relative to their non-fluorine-containing analogues) allows the fabrication of devices with larger device spacings. Light transmission through, e.g., a surface-stabilized ferroelectric device (as described in U.S. Pat. No. 4,367,924, the description of which is incorporated by reference herein) with two polarizers is represented by the following equation:

$$I=I_o (\sin^2(4\theta))(\sin^2(\pi\Delta nd/\lambda))$$

where $I_o$= transmission through parallel polarizers
$\theta$= material tilt angle
$\Delta n$= liquid crystal birefringence
d= device spacing
$\lambda$= wavelength of light used To maximize the transmission, both $\sin^2(4\theta)$ and $\sin^2(\pi\Delta nd/\lambda)$ must be at maximum. This occurs when each term equals one. The first term is a maximum when the tilt angle equals 22.5°. This is a function of the liquid crystal and is constant for a given material at a given temperature. The second term is maximum when $\Delta nd=\lambda/2$. This demonstrates the criticality of the low birefringence of the materials of this invention. Low birefringence allows a larger device thickness, d, for a given wavelength of light. Thus, a larger device spacing is possible while still maximizing transmission, allowing easier device construction.

The fluorine-containing liquid crystal compounds of the invention can be prepared by a process comprising the steps of (1) mixing at least one compound represented by the formula $$R\text{---}(M)_a\text{---}A\text{---}(N)_b\text{---}B'$$
$$\phantom{R\text{---}(M)_a\text{---}A}|\phantom{(N)_b\text{---}}|$$
$$\phantom{R\text{---}(M)_a\text{---}A}X_l\phantom{(N)_b\text{-}}Y_m$$

with at least one compound represented by the formula $$B''\text{---}(P)_c\text{---}D\text{---}R_f$$
$$\phantom{B''\text{---}(P)_c}|$$
$$\phantom{B''\text{---}(P)}Z_n$$

or (2) mixing at least one compound represented by the formula $$R\text{---}(M)_a\text{---}A'$$
$$\phantom{R\text{---}(M)_a}|$$
$$\phantom{R\text{---}(M)_a}X_l$$

with at least one compound represented by the formula $$A''\text{---}(N)_b\text{---}B\text{---}(P)_c\text{---}D\text{---}R_f$$
$$\phantom{A''\text{---}(N)_b}|\phantom{(P)_c\text{---}}|$$
$$\phantom{A''\text{---}(N)_b}Y_m\phantom{(P)_c}Z_n$$

where M, N, and P are each independently selected from the group consisting of

[ring structures: cyclohexyl, phenyl, naphthyl (various isomers), pyridyl, pyrimidyl, pyrazinyl, triazinyl, and dioxanyl ]

a, b, and c are each independently zero or an integer of from 1 to 3, with the proviso that the sum of a+ b+ c be at least 1;

each A and B are non-directionally and independently selected from the group consisting of a covalent bond, $$\text{---}\overset{O}{\underset{\|}{C}}\text{---}O\text{---},\ \text{---}\overset{O}{\underset{\|}{C}}\text{---}S\text{---},\ \text{---}\overset{O}{\underset{\|}{C}}\text{---}Se\text{---},$$

$$\text{---}\overset{O}{\underset{\|}{C}}\text{---}Te\text{---},\ \text{---}(CH_2CH_2)_k\text{---}\ \text{where k is 1 to 4,}$$

-continued $$\text{---}CH=CH\text{---},\ \text{---}C\equiv C\text{---},\ \text{---}CH=N\text{---},\ \text{---}CH_2\text{---}O\text{---},$$

$$\text{---}\overset{O}{\underset{\|}{C}}\text{---},\ \text{and}\ \text{---}O\text{---};$$

each A', A'', B', and B'' are independently selected from the group consisting of —OH, —COOH, —CH(CH$_2$OH)$_2$, —SH, —SeH, —the, —NH$_2$, —COCl, —CHO, —OSO$_2$R$_f'$, —OSO$_2$CH$_3$, —OSO$_2$-cyclo(C$_6$H$_4$)—CH$_3$, and —CH$_2$COOH, where R$_f'$ is a perfluoroalkyl group having from 1 to about 10 carbon atoms, and with the proviso that A' can enter into a coupling reaction with A'' and that B' can enter into a coupling reaction with B'';

each X, Y, and Z are independently selected from the group consisting of —H, —Cl, —F, —Br, —I, —OH, —OCH$_3$, —CH$_3$, —CF$_3$, —OCF$_3$ —CN, and —NO$_2$;

each l, m, and n are independently zero or an integer of 1 to 4;

D is selected from the group consisting of a covalent bond, $$\text{---}\overset{O}{\underset{\|}{C}}\text{---}O\text{---}C_rH_{2r}\text{---},\ \text{---}O\text{---}C_rH_{2r}\text{---},\ \text{---}O\text{---}\overset{O}{\underset{\|}{C}}\text{---}C_rH_{2r}\text{---},$$

$$\text{---}C\equiv C\text{---},\ \text{---}CH=CH\text{---},\ \text{---}\overset{O}{\underset{\|}{C}}\text{---},$$

$$\text{---}O\text{---}(C_sH_{2s}O)_t\text{---}C_rH_{2r'}\text{---},\ \text{---}C_rH_{2r}\text{---},\ \text{---}(C_sH_{2s}O)_t\text{---}C_rH_{2r'}\text{---},$$

$$\text{---}O\text{---},\ \text{---}S\text{---},\ \text{---}OSO_2\text{---},\ \text{---}SO_2\text{---},\ \text{---}SO_2\text{---}C_rH_{2r}\text{---},$$

$$\text{---}C_rH_{2r}\text{---}\underset{\underset{C_pH_{2p+1}}{|}}{N}\text{---}SO_2\text{---},\ \text{---}N(C_pH_{2p+1})\text{---},$$

$$\text{---}C_rH_{2r}\text{---}\underset{\underset{C_pH_{2p+1}}{|}}{N}\text{---}\overset{O}{\underset{\|}{C}}\text{---},\ \text{---}CH=N\text{---},$$

and combinations thereof, where r and r' are independently integers of 1 to about 20, s is independently an integer of 1 to about 10 for each (C$_s$H$_{2s}$O), t is an integer of 1 to about 6, and p is an integer of 0 to about 4;

R is selected from the group consisting of —O—((C$_{q'}$H$_{2q'-v'}$—R'$_{v'}$)—O)$_w$—C$_q$H$_{2q+1-v}$—R'$_v$, —((C$_{q'}$H$_{2q'-v'}$—R'$_{v'}$)$_v$—O)$_w$—C$_q$H$_{2q+1-v}$—R'$_v$, $$\text{---}\overset{O}{\underset{\|}{C}}\text{---}O\text{---}C_qH_{2q+1-v}\text{---}(R')_v,\ \text{---}O\text{---}\overset{O}{\underset{\|}{C}}\text{---}C_qH_{2q+1-v}\text{---}R'_v,$$

and $$\text{---}CR'\underset{(D)_{g'}}{\overset{(D)_g}{\diagup\hspace{-0.3em}\diagdown}}CR'\text{---}C_qH_{2q+1-v}\text{---}R'_v,$$

where each R' is independently selected from the group consisting of —Cl, —F, —CF$_3$, —NO$_2$, —CN, —H, —C$_q$H$_{2q+1}$,

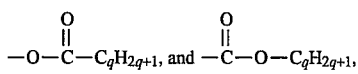

where q' is independently an integer of 1 to about 20 for each $(C_qH_{2q'}—O)$, q is an integer of 1 to about 20, w is an integer of 0 to about 10, v is an integer of 0 to about 6, each v' is independently an integer of 0 to about 6, g is an integer of 1, g' is an integer of 1, each D is independently selected from the group set forth above other than C≡C, with the proviso that R is chiral; and $R_f$ is $—(C_xF_{2x}O)_zC_yF_{2y+1}$, where x is independently an integer of 1 to about 10 for each $C_xF_{2x}O$, y is an integer of 1 to about 10, and z is an integer of 2 to about 10 (preferably, $R_f$ is linear, x is independently an integer of 1 to about 6 for each $(C_xF_{2x}O)$, y is an integer of 1 to about 6, and z is an integer of 2 to about 6);

and allowing said A' and A" or B' and B" to react, optionally in the presence of suitable coupling agent(s), i.e., reagent(s) which effect coupling.

Objects and advantages of this invention are further illustrated by the following examples, but the particular materials and amounts thereof recited in these examples, as well as other conditions and details, should not be construed to unduly limit this invention.

In the following examples, all temperatures are in degrees Centigrade and all parts and percentages are by weight unless indicated otherwise. Commercially available materials were chemically transformed by reaction pathways well-known to those skilled in the art and detailed in the examples. Chemical transformations were comprised of acylation, esterification, etherification, alkylation, and combinations thereof using fluorine-containing and non-fluorine-containing reactants to provide the precursor compounds, which, in turn, were caused to react together to yield the chiral, fluorine-containing liquid crystal compounds of this invention.

Compounds prepared in the various examples of this invention were characterized by their melting or boiling point, and structures were confirmed by using at least one of the following methods of analysis: chromatography; $^{13}C$-, $^1H$-, and $^{19}F$-NMR; and infrared and mass spectroscopies.

The 5-alkyl-2-(4-hydroxyphenyl)pyrimidines used in the examples were prepared using the method described by Zaschke, H. and Stolle, R. in "Synthese niedrigschmelzender Kristallin—Flüssiger Hetercyclen; 5-n-Alkyl-2-[4-n-alkanoyloxy-phenyl]pyrimidine" Z Chem. 15, 441–43 (1975).

EXAMPLES

Examples 1–17 describe procedures for preparing liquid crystal compounds of this invention. The chemical structure of each compound is given in Table 1.

Example 1

Preparation of
5-((S)-2-Chloro-4-methyl-pentanoyloxy)-2-(4-(1,1-dihydroperfluoro-2-(butoxyethoxy)ethoxy)phenyl)pyrimidine
(Compound 1, Table 1)

A 25 weight percent solution of sodium methoxide in methanol (82.5 ml, 0.36 moles) was added to a solution of 2-benzyloxytrimethinium perchlorate (30 g, 0.09 moles) (prepared according to the procedure of A. Holy and Z. Arnold, Collection Czechoslov. Chem. Commun. 38, 1372 (1973)), para-hydroxybenzamidine hydrochloride (15.6 g, 0.09 moles), and 500 ml of ethanol. The resulting mixture was heated to reflux overnight and then cooled to room temperature. Glacial acetic acid (75 ml) and 300 ml of water was added to the cooled mixture, resulting in the precipitation of product. The product was collected by filtration, washed with water, and air dried to give 23.06 g of 5-benzyloxy- 2-(4-hydroxyphenyl)pyrimidine.

Sodium hydride (1.7 g) was carefully added to a solution of 5-benzyloxy-2-(4-hydroxyphenyl)pyrimidine (18 g, 0.0647 moles) in 150 ml of N,N-dimethylformamide (DMF). The resulting solution was stirred for 15 minutes. 1,1-Dihydroperfluoro-2-(butoxyethoxy)ethoxy trifluoromethanesulfonate (36.5 g, 0.0647 moles) (prepared essentially as in Example 4 below) was then added, and the resulting mixture was heated to 95° C. for 1 hour. Upon cooling to room temperature, an equal volume of water was added to the cooled mixture. A solid precipitated and was collected by filtration. The solid was then slurried in boiling methanol, cooled to room temperature, and again collected by filtration. The collected solid was hydrogenated on a Parr™ Hydrogenator with catalytic 10% palladium on carbon in tetrahydrofuran under 60 psi (3100 torr) hydrogen pressure for approximately 18 hours. When the hydrogenation was complete, the catalyst was removed by filtration, and the solvent was removed on a rotary evaporator to yield 25.62 g of 5-hydroxy- 2-(4-(1,1-dihydroperfluoro-2-(butoxyethoxy)ethoxy)phenyl)pyrimidine.

Oxalyl chloride (1 ml, 2M in $CH_2Cl_2$) was added to a solution of 2-(S)-chloro-4-methylpentanoic acid (0.27g, 1.83 mmoles) in 5 ml of methylene chloride. One drop of DMF was added to the resulting solution, and bubbling was observed. The resulting mixture was stirred at room temperature for 1 hour, and the volatile material was then removed under vacuum on a rotary evaporator. The flask containing the remaining mixture was repressurized with dry nitrogen, and the resulting acid chloride was dissolved in 5 ml of methylene chloride. This solution was then added directly to a solution of 5-hydroxy-2-(4-(1,1-dihydroperfluoro- 2-(ethoxy)ethoxy)phenyl)pyrimidine (1 g, 1.66 mmoles) and pyridine (0.2 ml, 2.49 mmoles) in 5 ml of methylene chloride. The resulting mixture was stirred at room temperature overnight. Silica gel (5 g) was then added to the mixture, and the solvent was removed on a rotary evaporator. A product adsorbed onto the silica gel was then transferred to the top of a 50 g bed of silica gel. The product was eluted using a mixture of 20 parts by volume of hexane and 1 part by volume of ethyl acetate. The resulting white solid was recrystallized from methanol to yield 0.4 g of Compound 1, Table 1.

Example 2

Preparation of
5-(2-(S)-Chloropropanoyloxy)-2-(4-(1,1-dihydroperfluoro-2(hexyloxyethoxy)ethoxy)phenyl)pyrimidine
(Compound 2, Table 1)

This compound was prepared from 2-(S)-chloropropionic acid and 5-hydroxy-2-(4-(1,1-dihydroperfluoro- 2-(hexyloxyethoxy) ethoxy)phenyl)pyrimidine (prepared essentially as in Example 1 (which references Example 4) except substituting methyl perfluoro-2-(hexyloxyethoxy)acetate for methyl perfluoro-2-(butoxyethoxy)acetate in the preparation of the precursor alcohol according to Example 3 of U.S. Pat. No. 5,262,082 (Janulis et al.)) essentially as described in Example 1.

Example 3

Preparation of 5-(2-(S)-Chloropropanoyloxy)-2-(4-(1,1-dihydroperfluoro-4-(4butoxybutoxy)butoxy)phenyl)pyrimidine (Compound 3, Table 1)

This compound was prepared from 2-(S)-chloropropionic acid and 5-hydroxy-2-(4-(1,1-dihydroperfluoro- 4-(4-butoxybutoxy)butoxy)phenyl)pyrimidine (prepared essentially as in Example 1 (which references Example 4) except substituting methyl perfluoro-2-(butoxybutoxy)butyrate for methyl perfluoro-2(butoxyethoxy) acetate in the preparation of the precursor alcohol according to Example 3 of U.S. Pat. No. 5,262,082 (Janulis et al.)) essentially as described in Example 1.

Example 4

Preparation of 6-(1,1-Dihydroperfluoro-2-(butoxyethoxy)ethoxy)-2-(2-(S)chloropropanoyloxy)napthalene (Compound 4, Table 1)

650 g of 1,1-dihydroperfluorobutoxyethoxyethanol (prepared essentially as in Example 3 of U.S. Pat. No. 5,262,082 (Janulis et al.)) and 204 g of triethyl amine were mixed together in a flask fitted with a dry ice (-78° C) finger condenser, a thermometer, a dip tube for gas addition, and an overhead stirrer. The system was purged with dry nitrogen and was kept under slightly positive nitrogen pressure. With good stirring, the flask was cooled to −14° C. The nitrogen was then shut off, and 345 g of 91 weight percent trifluoromethanesulfonyl fluoride gas was added to the flask. The resulting reaction was allowed to run for two hours, and then 360 ml of water was added to the flask. The resulting crude product was washed with 360 ml of 3.5 weight percent HCl and 360 ml of water to give 872 g of washed, crude product. The washed product was distilled at a head temperature of 61°–78° C. (3.5 mm Hg, 3.5 torr) to give 772 g of 1,1-dihydroperfluoro- 2-(butoxyethoxy)ethoxy trifluoromethanesulfonate (92% yield).

6-Benzyloxy-2-napthol (2.5 g, 0.010 moles) was slowly added to 0.7 g of 60 weight percent sodium hydride in mineral oil suspended in 25 ml of dry dimethoxyethane. After stirring the resulting solution for 20 minutes at room temperature, the solution was cooled in an ice bath. 1,1-dihydroperfluoro-2-(butoxyethoxy) ethoxy trifluoromethanesulfonate (6.2 g, 0.011 moles) was then added slowly to the cooled solution. When the addition was complete, the ice bath was removed, and the resulting mixture was stirred at room temperature overnight. The solvent was then removed from the mixture under reduced pressure, and 25 ml of water and 25 ml of diethyl ether were added. After all solids had dissolved, the resulting aqueous and ether layers were separated, and the aqueous layer was extracted twice with 25 ml of diethyl ether. The ether layers were combined, washed three times with 20 ml of water, and dried with anhydrous magnesium sulfate, and the solvent was removed on a rotary evaporator. The resulting solid was dissolved in tetrahydrofuran and hydrogenated at 60 psi (3100 torr) in the presence of catalytic 10% palladium on carbon for 18 hours. When the hydrogenation was complete, the catalyst was removed by filtration, and the solvent was removed on a rotary evaporator. The resulting solid was recrystallized from hexane to yield 2.5 g of 6-( 1,1-dihydroperfluoro-2-(butoxyethoxy)ethoxy)-2-hyroxynapthalene.

Compound 4 was then prepared from 2-(S)-chloropropionic acid and 6-(1,1-dihydroperfluoro-2-(butoxyethoxy)ethoxy)- 2-hyroxynapthalene by essentially the esterification process described in Example 1.

Example 5

Preparation of 5-(1,1-Dihydroperfluoro-2-(butoxyethoxy)ethoxy)-2-(4-(S)-2-chloro-4-methylpentanoyloxy)phenyl)pyrimidine (Compound 5, Table 1)

To a solution of 5-benzyloxy-2-(4-hydroxyphenyl)pyrimidine (5g, 0.0180 moles) (prepared essentially as in Example 1) and imidazole (2.5g, 0.0360 moles) in N,N-dimethylformamide (DMF) (50 ml) was added 2.7 g (0.0180 moles) of t-butyldimethylsilylchloride. The resulting mixture was stirred at room temperature for 4 weeks. The stirred mixture was then poured into 100 ml of dilute bicarbonate, and the resulting solid was collected by filtration. After recrystallization from methanol, the solid was hydrogenated at 60 psi (3100 torr) with catalytic 10% palladium on carbon for 48 hours. The catalyst was then removed by filtration, and the solvent was removed on a rotary evaporator to yield 2.4 g of 5-hydroxy-2-(4-(t-butyldimethylsiloxyphenyl)pyrimidine.

The 2.4 g (0.0079 moles) of 5-hydroxy-2-(4-(t-butyldimethylsiloxyphenyl)pyrimidine was dissolved in 15 ml of DMF and treated with 0.2 g of sodium hydride. After stirring at room temperature for 5 minutes, 4.5 g (0.0079 moles) of 1,1-dihydroperfluoro- 2-(butoxyethoxy) ethoxy trifluoromethanesulfonate (prepared essentially as in Example 4) was added to the treated solution, and the resulting mixture was heated to 90° C. for 1 hour. After cooling to room temperature, the mixture was transferred to a separatory funnel with 50 ml of water and was extracted with two 20-ml aliquots of chloroform. The resulting chloroform layers were then combined and washed with two 20-ml aliquots of water, and the solvent was removed on a rotary evaporator. The resulting brown oil was chromatographed on silica gel (10:1 hexane:ethyl acetate) to give 2.5 g of 5-(1,1-dihydroperfluoro-2-(butoxyethoxy) ethoxy)-2-(4-t-butyldimethylsiloxyphenyl)pyrimidine.

The 5-(1,1-dihydroperfluoro-2-(butoxyethoxy)ethoxy)-2-(4-t-butyldimethylsiloxyphenyl)pyrimidine (2 g, 0.003 moles) was dissolved in 5 ml of tetrahydrofuran (THF) and treated with 4.2 ml of 1M tetrabutylammonium fluoride. After stirring the resulting mixture for 2 hours at room temperature, 10 ml of dilute aqueous ammonium chloride was added to the mixture. The mixture was then extracted three times with 5 ml aliquots of diethyl ether, and the resulting ether layers were combined and washed twice with 5 ml aliquots of water. The ether was removed from the mixture using a rotary evaporator to give a waxy, white solid. The solid was chromatographed on silica gel (using 5 volume percent methanol in chloroform as the eluent) to yield 1.09 g of 5-(1,1-dihydroperfluoro-2-(butoxyethoxy) ethoxy)-2( 4-hydroxyphenyl)pyrimidine.

Compound 5 was then prepared from S-2-chloro- 4-methylpentanoic acid and 5-(1,1-dihydroperfluoro- 2-(butoxyethoxy)ethoxy)-2-(4hydroxyphenyl)pyrimidine by essentially the esterification process described in Example 1.

Example 6

Preparation of 5-((S)-2-Chloropropoxy)-2-(4-(1,1-dihydroperfluoro-2-(butoxyethoxy)ethoxy)phenyl)pyrimidine (Compound 6, Table 1)

Sodium hydride (0.04 g, 1.7 mmoles) was added to a solution of 5-hydroxy-2-(4-(1,1-dihydroperfluoro-2-(butoxyethoxy) ethoxy) phenyl) pyrimidine (0.41 g, 1.7 mmoles) (prepared essentially as in Example 1 (which references Example 4)) in 5 ml of DMF and 5 ml of toluene. The resulting solution was stirred under a nitrogen atmosphere, and then 1-p-toluenesulfonoxy-2-(S)-chloropropane (0.41 g, 1.7 mmoles) was added to the solution by syringe. The resulting mixture was heated to 100° C. for 1 hour and then cooled to room temperature. The mixture was then poured into a separatory funnel with 50 ml of water and was extracted with three 10 ml aliquots of toluene. The resulting toluene layers were combined and washed with three 10 ml aliquots of water. The washed toluene layers were then concentrated under reduced pressure. The resulting solid was recrystallized from ethanol to yield 0.1 g of Compound 6, Table 1.

Example 7

Preparation of 4'-(1,1-Dihydroperfluoro-a-(2-(2-methoxyethoxy)ethoxy)ethoxy)-4-((S)-2chloropropanoyloxy)biphenyl (Compound 7, Table 1)

Sodium hydride (1.06 g, 60 weight percent in oil) was added to a solution of 4-4'-biphenol (6.6 g, 35.3 mmoles) in DMF (100 ml). The resulting solution was stirred under a nitrogen atmosphere for 0.5 hour and then heated to 60° C. 1,1-dihydroperfluoro-2-(2-(2-methoxyethoxy)ethoxy)ethoxy trifluoromethanesulfonate (9.4 g, 17.7 mmoles) (prepared essentially as in Example 1 (which references Example 4) except substituting methyl perfluoro-2-(methoxyethoxyethoxy)acetate for methyl perfluoro-2-(butoxyethoxy)acetate in the preparation of the precursor alcohol according to Example 3 of U.S. Pat. No. 5,262,082 (Janulis et al.)) was then added by syringe to the solution. The resulting mixture was stirred for 2 hours at 70° C. and then cooled to room temperature. The mixture was quenched with 100 ml of H$_2$O and extracted with three 100 ml aliquots of diethyl ether. The ether extracts were collected, dried (using MgSO$_4$), filtered, and concentrated. The resulting product was then purified by flash chromatography to give 6.5 g (65% yield) of 4'-(1,1-dihydroperfluoro-2( 2-(2-methoxyethoxy)ethoxy)ethoxy)-4-hydroxybiphenyl as a white solid having a melting point of 105°–107° C.

Compound 7 was then prepared from (S)-2-chloropropanoic acid and 4'-(1,1-dihydroperfluoro-2-(2-( 2-methoxyethoxy)ethoxy)ethoxy)-4-hydroxybiphenyl by essentially the esterification process described in Example 1. The resulting product was purified by column chromatography.

Example 8

Preparation of 4'-(1,1-Dihydroperfluoro-2-(2-butoxyethoxy)ethoxy)-4-)(S)-2-chloro-4methylpentanoyloxy)biphenyl (Compound 8, Table 1)

This compound was prepared from (S)-2-chloro- 4-methylpentanoic acid (prepared essentially by the method of T. Sierra et al., J. Am. Chem. Soc. 114, 7645 (1992)) and 4'-(1,1-dihydroperfluoro-2-(2-butoxyethoxy)ethoxy)- 4-hydroxybiphenyl (prepared essentially as in Examples 7 and 1) essentially as described in Example 7.

Example 9

Preparation of 4'-(1,1-Dihydroperfluoro-2-(2-butoxyethoxy)ethoxy)-4-((S)-2chloropropanoyloxy)biphenyl (Compound 9, Table 1)

This compound was prepared from (S)-2-chloropropionic acid and 4'-(1,1-dihydroperfluoro-2-(2butoxyethoxy)ethoxy)-4-hydroxybiphenyl (prepared essentially as in Examples 7 and 1) essentially as described in Example 7.

Example 10

Preparation of 4'-(1,1-Dihydroperfluoro-2-(2-butoxyethoxy)ethoxy)-4-((S)-2fluoropropanoyloxy)biphenyl (Compound 10, Table 1)

This compound was prepared from (S)-2-fluoropropionic acid and 4'-(1,1-dihydroperfluoro-2-(2-butoxyethoxy)ethoxy)- 4-hydroxybiphenyl (prepared essentially as in Examples 7 and 1) essentially as described in Example 7.

Example 11

Preparation of 4'-(1,1-Dihydroperfluoro-a-(2-butoxyethoxy)ethoxy)-4-((S)-2fluoropentanoyloxy)biphenyl (Compound 11, Table 1)

This compound was prepared from (S)-2-fluoropentanoic acid and 4'-(1,1-dihydroperfluoro-2-(2-butoxyethoxy)ethoxy)-4-hydroxybiphenyl (prepared essentially as in Examples 7 and 1) essentially as described in Example 7.

Example 12

Preparation of 4'-(1,1-Dihydroperfluoro-2-(2-butoxyethoxy)ethoxy)-4-((S)-2-chloropropoxy)biphenyl (Compound 12, Table 1)

This compound was prepared from (S)-1-p-toluenesulfonoxy- 2-chloropropane and 4'-(1,1-dihydroperfluoro- 2-(2-butoxyethoxy)ethoxy)-4-hydroxybiphenyl (prepared essentially as in Examples 7 and 1) essentially as described in Example 6, except that the resulting product was purified by column chromatography.

Example 13

Preparation of 4,-(1,1-Dihydroperfluoro-2-(2-butoxyethoxy)ethoxy)-4-((S,S)-2-chloro-3-methylpentanoyloxy)biphenyl (Compound 13, Table 1)

This compound was prepared from (S,S)-2-chloro- 3-methylpentanoic acid and 4'-(1,1-dihydroperfluoro-2-(2-butoxyethoxy) ethoxy)-4-hydroxybiphenyl (prepared essentially as in Examples 7 and 1) essentially as described in Example 7.

Example 14

Preparation of 4-(1,1-Dihydroperfluoro-2-(2-butoxyethoxy)ethoxy)phenyl-(S)-4-methylhexyloxy benzoate (Compound 14, Table 1)

960 mg of 4-(1,1-dihydroperfluoro-2-(2-butoxyethoxy)ethoxy)phenol (1.83 mmoles) (prepared essentially as in Example 6 of U.S. Pat. No. 5,262,082 (Janulis et al.)) was weighed into a vial and dissolved in 5 ml dichloromethane and 2 ml (approximately 1.5 g) of triethylamine. One equivalent, 432 mg, of 4-(S)- 4-methylhexyloxy benzoic acid was weighed into a 25 ml 3-necked flask, dissolved under nitrogen in 10 ml dichloromethane, treated with 0.23 g of oxalyl chloride, and stirred overnight. The phenol solution was then added to the flask by syringe. The resulting mixture was stirred for 15 minutes, then washed with water which was made acidic by the dropwise addition of glacial acetic acid, and washed again with saturated sodium chloride solution. The resulting organic phase was dried over magnesium sulfate and filtered through a short column of silica gel (5 g) using dichloromethane as the eluent. Solvent was then removed from the filtered phase under vacuum using a rotary evaporator, and the resulting product was recrystallized from ethanol several times at $-20°$ C. to yield 1.00 g of Compound 14, Table 1.

Example 15

Preparation of 4-(1,1-Dihydroperfluoro-2-(2-butoxyethoxy)ethoxy)phenyl-4-(4-((S)-2-methylbutoxy)phenyl) benzoate (Compound 15, Table 1)

4-(4-((S)-2-methylbutoxy)phenyl) benzoic acid (1.00 g) was weighed into a 50 ml flask and treated with 5 ml (approximately 8.2 g) of thionyl chloride at reflux for 15 minutes. Excess thionyl chloride was distilled, and the last traces of thionyl chloride were removed by heating under a nitrogen flow to yield crude acid chloride. 4-(1,1-Dihydroperfluoro-2-(2-butoxyethoxy)ethoxy)phenol (1.94 g, 1.05 eq) (prepared essentially as in Example 6 of U.S. Pat. No. 5,262,082 (Janulis et al.)) was weighed into a vial, diluted with 25 ml dichloromethane, and treated with 10 ml (approximately 7.2 g) of triethylamine. The resulting solution was added to the crude acid chloride, and the resulting mixture was allowed to stand for 15 minutes. The mixture was washed once with 50 ml water which was made acidic by the dropwise addition of glacial acetic acid and once with 50 ml of saturated sodium chloride solution. The resulting organic phase was dried over magnesium sulfate and filtered through a short column of silica gel (10 g) using dichloromethane as the eluent. Solvent was removed from the filtered phase, and the resulting product was column chromatographed on silica gel (using toluene as the eluent) and recrystallized from ethanol to yield 0.445 g of Compound 15, Table 1.

Example 16

Preparation of 4-(1,1-Dihydroperfluoro-a-(2-butoxyethoxy)ethoxy)phenyl-4-((S)-2-chloropropoxy) benzoate (Compound 16, Table 1) Methyl 4-((S)-2-chloropropoxy) benzoate (S)-2-Chloro-1-propanol (Aldrich Chemical Co., 1.00 g, 10.6 mmoles), methyl 4-hydroxy benzoate (1.81 g, 1.1 eq), triphenylphosphine (4.13 g, 1.5 eq), and 25 ml dry tetrahydrofuran were charged to a 50 ml 3-necked flask under nitrogen. Diethyl azodicarboxylate (2.9 g, 1.6 eq) was then added to the flask by syringe. The resulting solution was stirred for 3 days and then poured into a mixture of 250 ml water and 25 ml ethyl acetate. The resulting mixture was shaken, the resulting aqueous and organic phases were separated, and the aqueous phase was extracted once more with 25 ml ethyl acetate. The resulting organic phases were combined, dried over magnesium sulfate, and filtered. The solvent was then removed from the filtered phases, and the resulting crude product was dissolved in dichloromethane and passed through silica gel. Upon removal of solvent under vacuum, reaction by-products began to crystallize. Gas chromatography (GC) showed the resulting supernatant to be mostly the desired product, so the byproducts were recrystallized from cyclohexane to recover traces of product. The resulting supernatants were combined and passed through silica gel using cyclohexane as the eluent, and the solvent was removed under vacuum to recover partially purified product which was hydrolyzed without further purification.

4-((S)-2-Chloropropoxy) Benzoic Acid

The resulting crude methyl 4-((S)-2-chloropropoxy) benzoate was dissolved in 25 ml of dimethylsulfoxide and treated with 0.44 g (approximately 1.04 eq) of sodium hydroxide in 25 ml water. The resulting reaction was monitored by GC, and, at one hour, an additional portion of 0.44 g solid sodium hydroxide was added to the resulting mixture. An aliquot of the mixture taken 45 minutes later showed the absence of starting material, so the mixture was poured into 50 ml 0.1 N hydrochloric acid. Organics were extracted from the resulting mixture with two 50 ml portions of ethyl acetate and were dried over magnesium sulfate, filtered, and the solvent removed under vacuum to yield a crude solid product acid that was recrystallized from 20 ml ethanol at $-20°$ C. The product acid was collected and dried under vacuum.

4-(1,1-Dihydroperfluoro-2-(2-butoxyethoxy)ethoxy)phenyl-4,-((S)-2-chloropropoxy) benzoate The dried product acid was charged to a 100 ml flask, dissolved in 25 ml dichloromethane, and treated with 3.7 ml (5.2 g) oxalyl chloride under nitrogen. After stirring for 10 minutes, the dichloromethane was distilled at atmospheric pressure, and excess oxalyl chloride was removed under vacuum. The resulting acid chloride was dissolved in 25 ml dichloromethane and treated with a solution of 5.8 g 4-(1,1-dihydroperfluoro-2- (2-butoxyethoxy) ethoxy) phenol (prepared essentially as in Example 6 of U.S. Pat. No. 5,262,082 (Janulis et al.)) (1.05 eq based on 2-(S)-chloropropanol), 7 ml (approximately 5.0 g) triethylamine, and 25 ml dichloromethane. After stirring the resulting mixture for 15 minutes, the mixture was washed with 100 ml water and with 100 ml saturated sodium chloride solution. After drying of the washed mixture over magnesium sulfate, the mixture was filtered, solvent and excess triethylamine were removed under vacuum, and the remaining material was passed through 5 g of silica gel using dichloromethane as the eluent. The resulting product was recrystallized twice, once from 25 ml methanol at 4° C., then from 20 ml ethanol at −20° C., to yield 0.262 g of purified Compound 16, Table 1.

Example 17

Preparation of 4-((S,S)-2,3-Epoxy)-hexyloxyphenyl-4-(1,1-dihydroperfluoro-a-(2-butoxyethoxy)ethoxy) benzoate (Compound 17, Table 1)

4-((S,S)-2,3-epoxy)-hexyloxy phenol (Displaytech WP46, 1.00 g, 4.82 mmoles) was weighed into a 100 ml flask equipped with a magnetic stirrer, a septum, and a nitrogen atmosphere. The phenol was dissolved in 25 ml dichloromethane. One equivalent of 4-(1,1-dihydroperfluoro-2-(2-butoxyethoxy)ethoxy) benzoyl chloride (2.76 g) (prepared essentially as in Example 11 of U.S. Pat. No. 5,262,082 (Janulis et al.) (except substituting 4-(1,1-dihydroperfluoro-2-(2-butoxyethoxy)ethoxy) trifluoromethanesulfonate for 1,1-dihydroheptafluoro- 2-ethoxyethyl triflate) with conversion of the resulting acid to the corresponding acid chloride essentially by the method of Example 16 supra) was weighed into a vial and dissolved in 5 ml dichloromethane. 2.0 ml of triethylamine (excess, approximately 3 eq) was added to the solution of the epoxy phenol, followed immediately by addition of the acid chloride solution (both additions being by syringe). After 20 minutes, the resulting mixture was washed with four 100 ml portions of water and one 100 ml portion of saturated sodium chloride solution, and the washed mixture was dried over sodium sulfate overnight. The dried mixture was filtered, the solvent was removed under vacuum, and the resulting crude product was purified by chromatography on neutral silica using toluene as the eluent. Combined fractions that showed product by thin layer chromatography were recrystallized from toluene and dried under vacuum to yield 0.405 g of Compound 17, Table 1.

TABLE 1

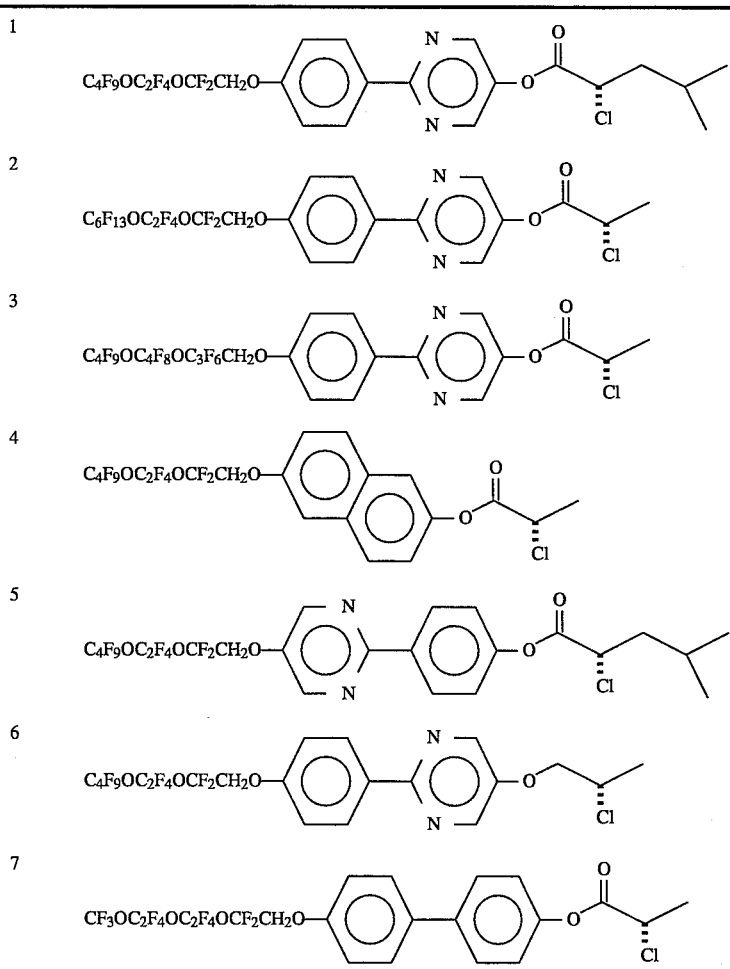

TABLE 1-continued

| Compound No. | Structure |
|---|---|
| 8 | 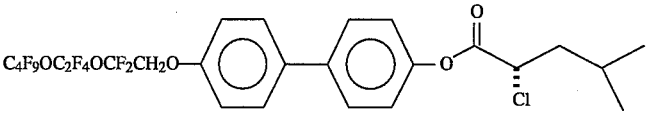 |
| 9 | 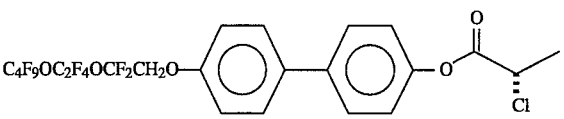 |
| 10 | 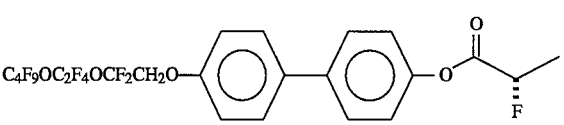 |
| 11 | 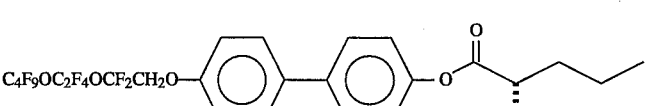 |
| 12 | 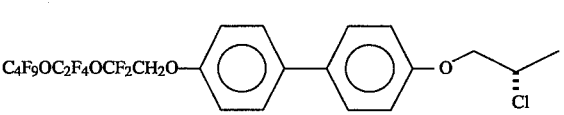 |
| 13 | 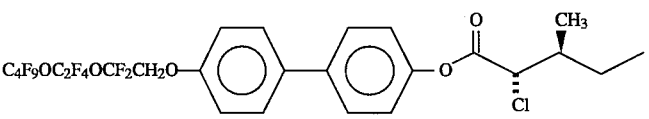 |
| 14 | 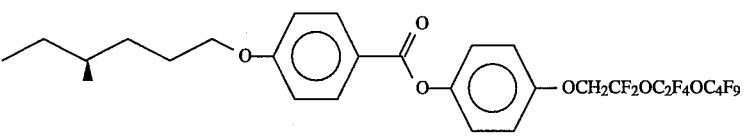 |
| 15 | 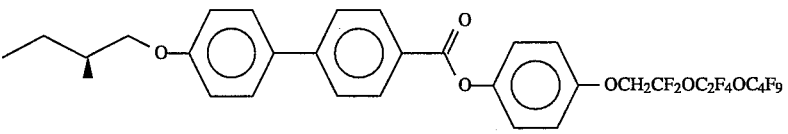 |
| 16 | 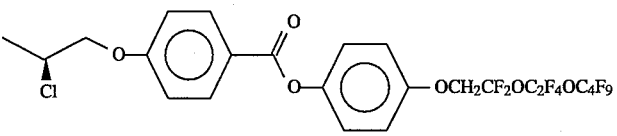 |
| 17 | 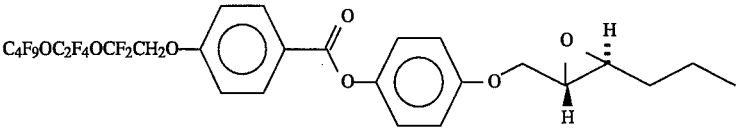 |

The compounds of Table 1 were evaluated for transition temperatures by optical observation of material phase changes using a Linkam TMH600 hot stage and a Zeiss polarizing microscope. The transition temperatures (°C.) were obtained upon cooling from the isotropic state (I) and are set forth in Table 2.

TABLE 2

Mesophase Characterization for Compounds Listed in Table 1

| Compound No. | I to $S_A$ | to M | to K | mp |
|---|---|---|---|---|
| 1 | 53 | 25 | | |
| 2 | 121 | 53 | | |
| 3 | 124 | 48 | | |
| 4 | 55 | 28 | | |

TABLE 2-continued

Mesophase Characterization for Compounds Listed in Table 1

| Compound No. | I to $S_A$ | to M | to K | mp |
|---|---|---|---|---|
| 5 | — | — | — | 64–66 |
| 6 | 111 | 20 | 15 | |
| 7 | 136.7 | 67.8 | | |
| 8 | 65 | — | 28 | |
| 9 | 129 | 91 | | |
| 10 | 158 | 120 | | |
| 11 | 115 | 59 | | |
| 12 | 100 | 75 | | |
| 13 | 76.9 | 5.3 | | |
| 14 | 73.3 | −8.8 | | |
| 15 | >191 | 86.8 | | |
| 16 | 110 | 51.6 | | |
| 17 | 113.7 | 45.9 | | |

I = Isotropic,
$S_A$ = Smectic A,
M = Higher order mesophase,
K = Crystalline,
mp = melting point Examples 18 and 19 describe liquid crystal compound mixtures and liquid crystal display devices of this invention.

Example 18

A device utilizing a chiral compound (Compound 10) of this invention was constructed as follows. Onto an indium tin oxide (ITO) coated (300 Å ITO coating) glass substrate (2.85 cm wide, 3.5 cm long, 0.1 cm thick) which had been ultrasonically cleaned was placed several drops of a 0.52 weight percent solution of nylon 6/6 (Aldrich Chemical Co., Inc.) in formic acid. The substrate was spun at 1200 rpm for 40 seconds and cured at 75° C. for 16 hours to provide a nylon coating about 400 Å thick. The coated plate was rubbed (20 strokes) in one direction with a 115 gram rubbing bar (a glass rod 2.5 cm in diameter, 10 cm long) about which a 65% cotton, 35% rayon velveteen fabric (J. B. Martin Co., #5100 Matinee) with the pile side out was tightly wrapped, to provide an oriented alignment layer on the substrate.

Onto another ITO-coated (300 Å ITO coating) glass substrate (2.85 cm wide, 3.5 cm long, 0.1 cm thick) having a pattern of polyimide spacer posts 1.5 μm in height and which had been ultrasonically cleaned was placed several drops of a 1.5 weight percent solution of polymethylsiloxane (5.6% GR-651L, available from Owens-Illinois, Inc.) in butyl alcohol. The substrate was spun at 8000 rpm for 20 seconds and cured at 75° C. for 16 hours to provide an alignment coating about 200–300 Å thick.

The substrates were assembled using a UV curable adhesive (Norland™ 61 Optical Adhesive, available from Norland Products, Inc.) with the ITO-constituted electrodes and the alignment layers facing inward to form a device. The device was then filled with the following mixture of liquid crystal compounds using capillary action under vacuum:

$C_{10}H_{21}$—(pyrazine ring)—(phenyl)—$OCH_2C_3F_6OC_4F_8OC_4F_9$ 49.0wt%

$C_8H_{17}$—(pyrazine ring)—(phenyl)—$OCH_2C_3F_6OC_4F_8OC_4F_9$ 12.3wt%

$C_8H_{17}$—(pyrazine ring)—(phenyl)—$OCH_2CF_2OC_2F_4OC_6F_{13}$ 12.3wt%

$C_8H_{17}$—(pyrazine ring)—(phenyl)—$OCH_2CF_2OC_2F_4OC_4F_9$ 4.1wt%

$C_{10}H_{21}$—(pyrazine ring)—(phenyl)—$OCH_2CF_2OC_2F_4OC_6F_{13}$ 4.1wt%

$C_{10}H_{21}$—(pyrazine ring)—(phenyl)—$OCH_2CF_2OC_2F_4OC_4F_9$ 4.1wt%

$C_8H_{17}$—(pyrazine ring)—(phenyl)—$OCH_2CF_2OC_2F_4OC_2F_4OCF_3$ 4.1wt%

$C_4F_9OC_2F_4OCF_2CH_2O$—(phenyl)—(phenyl)—$O-C(=O)-CH(F)(CH_3)$ 10.0wt%

The phase transition temperatures for the mixture were measured essentially as described above for Table 2 and found to be:

| | |
|---|---|
| I to $S_A$ | 79.4° C. |
| $S_A$ to $S_C$ | 43.5° C. |
| $S_C$ to M | −10.2° C. |

The phase transition temperatures for the achiral base mixture (i.e., the above mixture without the last-listed (chiral) compound) were measured essentially as described above for Table 2 and found to be:

| | |
|---|---|
| I to $S_A$ | 85.5° C. |
| $S_A$ to $S_C$ | 51.0° C. |

| | |
|---|---|
| $S_C$ to M | −6.4° C. |

The ITO-constituted electrodes of the device were connected to an arbitrary waveform generator with variable output voltage. Optical transmission was measured by placing the device on a rotating stage between two crossed polarizers, with the polarizer/device combination placed between a collimated, incandescent light source of about 1 mW intensity (5 mm diameter) and a silicon photodetector. The incandescent light source was filtered to confine its wavelength spectrum to between 450 and 700 nm. The output from the photodetector was monitored on an oscilloscope. The latching time for the device, measured with a field of 20 V/μm and at a temperature of 38.5° C., was 167 μs. The device was driven with a voltage waveform consisting of bipolar, square pulses of 20 V/μm amplitude, spaced 30 mS apart by a train of square pulses having the same width and 6.7 V/μm amplitude. The latching time was taken to be the minimum pulse width needed to observe two stable and saturated, multiplexed memory states.

The polarization of the device was determined essentially as described by Miyasato et al. in Jap. *J. Appl. Phys.* 22, 661 (1983) and found to be 12.5 nC/cm² at 38.5° C.

The memory to tilt angle ratio ($\emptyset_m/\emptyset_t$) for the device was 0.97. The device was driven with a 30 Hertz square wave of 20 volt amplitude. The tilt angle, $\emptyset_t$, was taken to be half the angle separating the extinction points of the driven states. To obtain the memory angle, $\emptyset_m$, the device was driven with a voltage waveform consisting of alternating bipolar, square pulses of 20 V/μm amplitude, spaced about 30 ms apart. The pulse width was adjusted to observe two stable and saturated memory states. The memory angle was taken to be half the angle separating the extinction points of the two memory states.

Example 19

A device was prepared essentially as in Example 18. The device was filled with a liquid crystal mixture which was as described in Example 18, except that Compound 5 was used as the chiral dopant in place of Compound 10.

The phase transition temperatures for the mixture were measured essentially as described above for Table 2 and found to be:

| | |
|---|---|
| I to $S_A$ | 76.3° C. |
| $S_A$ to $S_C$ | 35.6° C. |
| $S_C$ to M | −3.3° C. |

The latching time for the device, measured essentially as in Example 18 with a field of 20 V/μm and at a temperature of 25.6° C., was 130 μs. The polarization of the device was determined essentially as in Example 18 and found to be 11.6 nC/cm² at 25.6° C. The memory to tilt angle ratio ($\emptyset_m/\emptyset_t$) was determined essentially as in Example 18 and found to be 0.98.

COMPARATIVE EXAMPLE

A device was prepared essentially as in Example 18. The device was filled with a liquid crystal mixture which was as described in Example 18 except that a mixture of 2 parts by weight of comparative compound C1 and 1 part by weight of comparative compound C2 (the compounds having the structures shown below) was substituted for Compound 10.

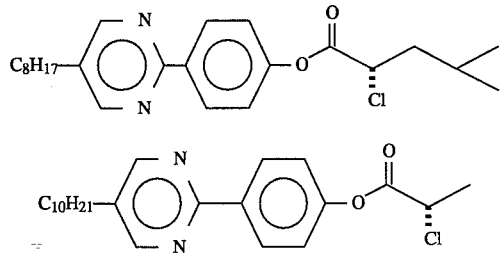

The phase transition temperatures for the mixture were measured essentially as described above for Table 2 and found to be:

| | |
|---|---|
| I to $S_A$ | 85.5° C. |
| $S_A$ to $S_C$ | 30.6° C. |
| $S_C$ to M | −6.4° C. |

The latching time for the device, measured essentially as in Example 18 with a field of 20 V/μ and at a temperature of 20.6° C., was 24.7 μs. The polarization of the device was determined essentially as in Example 18 and found to be 17.1 nC/cm² at 20.6° C. The memory to tilt angle ratio ($\emptyset_m/\emptyset_t$) for the device was determined essentially as in Example 18 and found to be 0.84. A comparison of this data with that given above for Examples 18 and 19 shows that compounds of this invention, when used in admixture with achiral, fluoroether-containing liquid crystal compounds, provide mixtures which exhibit higher memory to tilt angle ratios than mixtures of the same achiral compounds with chiral, hydrocarbon liquid crystal compounds. In addition, this comparison indicates that compounds of the invention show only a minimal effect on the smectic C temperature range of such mixtures.

Examples 20–25 describe procedures for preparing liquid crystal compounds of this invention. The chemical structure of each compound is given in Table 4.

Example 20

Preparation of
5-((S)-2—Fluorodecyloxy)-2-(4-(1,1-dihydroperfluoro-2-(butoxyethoxy)ethoxy)phenyl)pyrimidine
(Compound 18, Table 4)

2-(S)-fluorodecanol (800 mg, 4.5 mmoles; which can be prepared by the procedure described by H. Nohira et al. in Mol. Cryst. Liq. Cryst. 180B, 379–88 (1990)) was combined with toluene sulfonyl chloride (865 mg, 4.5 mmoles), ethyl diisopropyl amine (1165 mg, 9 mmoles), and dimethylaminopyridine (27 mg, 0.22 mmoles) in methylene chloride (20 mL). The resulting mixture was stirred at room temperature overnight. The resulting crude tosylate product was purified by flash chromatography on silica gel, eluting with 10 parts by volume of hexane and 1 part by volume of ethyl acetate.

A three-necked flask equipped with a magnetic stir bar, a condenser, and a nitrogen inlet was charged with potassium carbonate (85 mg, 0.6 mmoles) and acetonitrile (20 mL). With stirring, 5-hydroxy-2-(4-(1,1-dihydroperfluoro- 2-(butoxyethoxy)ethoxy)phenyl)pyrimidine (364 mg, 0.6 mmole; prepared essentially as in Example 1 above) was slowly added to the resulting mixture. The mixture was stirred at room temperature for 30 minutes. 1-p-toluenesulfonoxy-2-(S)-fluorodecane (200 mg, 0.6 mmoles) was then added to the stirred mixture. The mixture was heated to reflux overnight and then poured into a separatory funnel containing water (–20 mL). The resulting layers were separated, and the aqueous phase was extracted with diethyl ether and purified by chromatography (essentially as in Example 1 above), eluting with 10 parts by volume of hexane and 1 part by volume of ethyl acetate. The yield of desired product was 0.35 g. The structure of the product was confirmed by $^1$H and $^{19}$F nuclear magnetic resonance spectroscopy.

Example 21

Preparation of 5- (1,1-Dihydroperfluoro (2-(2-butoxyethoxy) ethoxy))-2-(4-(dihydro-5-(R)-oxymethyl- 3- (R) -hexyl-2 (3H) -furanone) phenyl) pyrimidine (Compound 19, Table 4)

5-Benzyloxy-2-(4-hydroxyphenyl)pyridine (7.5 g, 26.95 mmoles) was combined with (R)-epichlorohydrin (9.97 g, 107.8 mmoles) and potassium t-butoxide (29.6 mL of a 1M solution in t-butanol). The resulting mixture was heated to 60° C. for three hours under nitrogen. The mixture was then poured into saturated brine and was extracted with two 200 mL aliquots of chloroform. The combined chloroform extracts were washed with water and then dried over sodium sulfate. The solvent was removed from the extracts under reduced pressure, and the resulting crude product was recrystallized from acetonitrile to yield the epoxide, 5-benzyloxy-2-(4-(2-(R)-epoxy)propoxy)phenyl)pyridine. This epoxide (5.9 g, 18.42 mmoles) was combined with hexylmalonate (6.36 g, 27.6 mmoles) and potassium t-butoxide (22.1 mL of a 1M solution in t-butanol) in t-butanol (20 mL). The resulting mixture was heated to reflux for two hours and was then cooled and acidified to a pH of 1 with dilute HCl. The mixture was filtered, washed with water and then with methanol, and air-dried to yield the crude dihydrofuranone as a mixture of cis and trans isomers. A portion of this mixture (2.7 g) was resolved by preparative high pressure liquid chromatography, eluting with hexane/chloroform/ ethyl acetate (45:50:5), to yield a fraction that was 93:7 cis/trans (0.67 g). This fraction (predominately cis) was hydrogenated essentially as in Example 1 for three hours to remove the benzyl protecting group.

The hydrogenated product, 5-hydroxy-2-(4-(dihydro-5-(R)-oxymethyl-3-(R)-hexyl-2(3H)-furanone)phenyl)pyrimidine, (0.44 g, 1.19 mmoles) was combined with potassium carbonate (0.20 g, 1.43 mmoles) and 1,1-dihydroperfluoro-2-(butoxyethoxy)ethyl trifluoromethanesulfonate (0.74 g, 1.31 mmoles; prepared essentially as in Example 4 above) in acetonitrile (10 mL), and the resulting mixture was refluxed for 1.5 hours. After cooling, water (10 mL) was added to the mixture, and the mixture was then filtered. The filtrate was washed with water and then with methanol, and the washed filtrate was air-dried. The resulting crude product was then further purified by column chromatography on silica gel, eluting with chloroform, to yield 5-(1,1-dihydroperfluoro(2-(2-butoxyethoxy)ethoxy))- 2-(4-(dihydro-5-(R)-oxymethyl-3-(R)-hexyl-2(3H)-furanone) phenyl)pyrimidine. The yield of the desired product was 0.57 g. The structure of the product was confirmed by $^1$H and $^{19}$F nuclear magnetic resonance spectroscopy.

Example 22

Preparation of 5-(1,1-Dihydroperfluoro-(6-(2-butoxyethoxy)hexyloxy))-2-(4-(dihydro-5-(R)-oxymethyl-3-(R)-hexyl-2(3H)-furanone)phenyl)pyrimidine (Compound 20, Table 4)

Using essentially the procedure of Example 21, 5-hydroxy-2-(4-(dihydro-5-(R)-oxymethyl-3-(R)-hexyl- 2(3H)-furanone)phenyl)pyrimidine (0.70 g, 1.89 mmoles) was combined with potassium carbonate (0.31 g, 2.27 mmoles) and 1,1-dihydroperfluoro-6-(butoxyethoxy)hexyl nonafluorobutanesulfonate (1.73 g, 1.89 mmoles) in acetonitrile (20 mL). [The 1,1-dihydroperfluoro-6-(butoxyethoxy)hexyl nonafluorobutanesulfonate had been prepared from nonafluorobutanesulfonyl fluoride (which can be prepared by the methods described by P.M. Savu in *Kirk-Othmer Encyclopedia of Chemical Technology*, Fourth Edition, Volume 11, pages 558–64, John Wiley & Sons, New York (1994)) and 1,1-dihydroperfluoro-2-(butoxyethoxy)hexanol (prepared by sodium borohydride reduction of the corresponding methyl ester, essentially as described in Example 3 of U.S. Pat. No. 5,262,082 (Janulis et al.)) by essentially the method described in Example 4 above.] The resulting crude product was isolated and purified essentially as in Example 21 to yield 1.10 g of a 90:10 mixture of cis/trans dihydrofuranone isomers (as determined by $^1$H nuclear magnetic resonance spectroscopy).

Example 23

Preparation of 5-(1,1-Dihydroperfluoro-(4-(4-butoxybutoxy)butoxy))-2-(4-(dihydro-5-(R)-oxymethyl-3-(R)-hexyl-2(3H)-furanone)phenyl)pyrimidine (Compound 21, Table 4)

Using essentially the procedure of Example 21, 5-hydroxy-2-(4-(dihydro-5-(R)-oxymethyl-3-(R)-hexyl-2(3H)-furanone)phenyl)pyrimidine (0.70 g, 1.89 mmoles) was combined with potassium carbonate (0.31 g, 2.27 mmoles) and 1,1-dihydroperfluoro-4-(butoxybutoxy)butyl trifluoromethanesulfonate (1.73 g, 1.89 mmoles; prepared from 1,1-dihydroperfluoro-4-(4-butoxybutoxy)butanol essentially as in Example 4 above) in acetonitrile (20 mL). The resulting crude product was isolated and purified essentially as in Example 21 to yield 1.05 g of a 90:10 mixture of cis/trans dihydrofuranone isomers (as determined by $^1$H nuclear magnetic resonance spectroscopy).

Example 24

Preparation of 4-(1,1-Dihydroperfluoro-2-(2-(2-methoxyethoxy)ethoxy)ethoxy)-4'-(dihydro-5-(R)-oxymethyl-2(3H)furanone)biphenol (Compound 22, Table 4)

4-(1,1-dihydroperfluoro-2-(2-(2-methoxyethoxy) ethoxy) ethoxy)-4'-biphenol (2 g, 35 mmoles; prepared essentially as in Example 7 above) and (S)-(+)-dihydro-5-(p-tolylsulfonyloxymethyl)-2(3H)furanone (available from Aldrich Chemical Co., 1.0 g, 37 mmoles) were dissolved in dry acetonitrile (20 mL). Potassium carbonate (0.51 g, 37 mmoles) was added and slurried into the resulting mixture. This mixture was heated for 5 hours at 70°–85° C. and was then cooled to room temperature. Water (60 mL) was added to the cooled mixture. The resulting solid product was collected by filtration and recrystallized from methanol to give 0.53 g of a white solid. The structure of the product was confirmed by $^1$H and $^{19}$F nuclear magnetic resonance spectroscopy.

Example 25

Preparation of
5-(6-(1,1-Dihydroperfluoro(((2-methoxyethoxy) ethoxy) ethoxy) hexyloxy-2-(4-(dihydro-5-(R)-oxymethyl-3-(R)-hexyl-2(3H)-furanone)phenyl)pyrimidine (Compound 23, Table 4)

Into a flask fitted with a stirrer, a thermometer, and a reflux condenser was charged KOH (24.6 g, 373 mmoles, dissolved in 25 mL water), 1,1-dihydroperfluoromethoxyethoxyethanol (50 g, 125.6 mmoles; prepared by sodium borohydride reduction of the corresponding methyl ester, essentially as described in Example 3 of U.S. Pat. No. 5,262,082 (Janulis et al.)), tetrabutylammonium hydrogen sulfate (3.0 g, 8.8 mmoles), and 1,6-dibromohexane (150 g). The resulting reaction mixture was heated at 100° C. for three hours, cooled to room temperature, and diluted with water (75 mL) and perfluoro-N-methyl morpholine (153 g) in a separatory funnel. The resulting lower fluorochemical phase was removed from the funnel, and the solvent was distilled at ambient pressure. The resulting residue was distilled, and the fraction boiling at 83°–97° C. at 0.3 torr was collected. GC/MS analysis of this fraction showed that it contained 12 area % dibromohexane, 71 area % desired 6-(1,1-dihydroperfluoro(methoxyethoxyethoxyethoxy))-1-bromohexane ($CF_3O(CF_2CF_2O)_2CF_2CH_2O(CH_2)6Br$), and 7 area % $CF_3O(CF_2CF_2O)_2CF_2CH_2O(CH_2)_6OCH_2CF_2(OCF_2CF_2)_2 OCF_3$.

Using essentially the procedure of Example 21, 5-hydroxy-2-(4-(dihydro-5-(R)-oxymethyl-3-(R)-hexyl- 2(3H)-furanone)phenyl)pyrimidine (0.20 g, 0.54 mmoles) was combined with potassium carbonate (0.09 g, 0.65 mmoles) and 6-(1,1-dihydroperfluoro(methoxyethoxyethoxyethoxy))- 1-bromohexane (0.30 g, 0.54 mmoles) in acetonitrile (20 mL). The resulting crude product was isolated and purified essentially as in Example 21 to yield 0.18 g of a 90:10 mixture of cis/trans dihydrofuranone isomers (as determined by $^1$H nuclear magnetic resonance spectroscopy).

The compounds of Examples 20–24 were evaluated for transition temperatures by differential scanning calorimetry (DSC) and/or by optical observation of material phase changes using a Linkam TMH600 hot stage and a polarizing microscope. The transition temperatures (°C.) were obtained upon cooling from the isotropic state (I) to the smectic A mesophase ($S_A$) and to higher order mesophases (M1 and M2) and are set forth in Table 3.

TABLE 3

| Mesophase Characterization for Compounds Listed in Table 4 | | | | |
|---|---|---|---|---|
| Compound No. | I to $S_A$ | $S_A$ to M1 | M1 to M2 | Melting Point |
| 18 | 85 | 65 | 47 | |
| 19 | | | | 130–131 |
| 20 | 177 | 138 | | |
| 21 | 157 | 141 | | |
| 22 | | | | 126 |
| 23 | 116 | 113 | | |

TABLE 4

Compound Number  Structure

18

19

20

TABLE 4-continued

| Compound Number | Structure |
|---|---|
| 21 | $C_4F_9OC_4F_8OC_3F_6CH_2O$—[pyridine]—[phenyl]—O—CH$_2$—[tetrahydrofuranone]—$C_6H_{13}$ |
| 22 | $CF_3OC_2F_4OC_2F_4OCF_2CH_2O$—[phenyl]—[phenyl]—O—CH$_2$—[tetrahydrofuranone] |
| 23 | $CF_3O(C_2F_4O)_2OCF_2CH_2O(CH_2)_6O$—[pyridine]—[phenyl]—O—CH$_2$—[tetrahydrofuranone]—$C_6H_{13}$ |

Various modifications and alterations of this invention will become apparent to those skilled in the art without departing from the scope and spirit of the invention.

We claim:

1. Fluorine-containing, chiral liquid crystal compounds represented by the general formula (I):

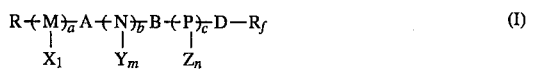

where M, N, and P are each independently selected from the group consisting of

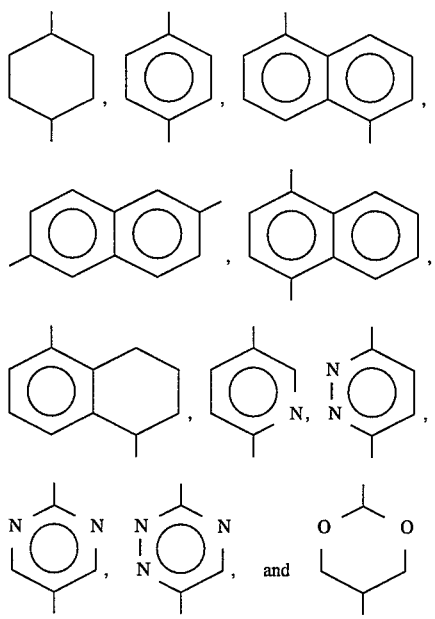

a, b, and c are each independently zero or an integer of from 1 to 3, with the proviso that the sum of a+ b+ c be at least 1;

each A and B are non-directionally and independently selected from the group consisting of a covalent bond,

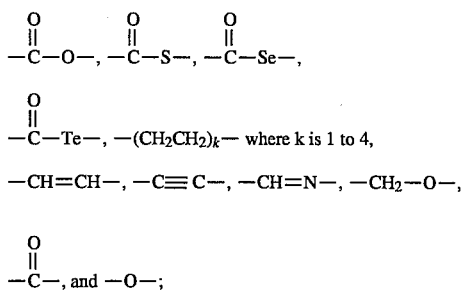

each X, Y, and Z are independently selected from the group consisting of —H, —Cl, —F, —Br, —I, —OH, —OCH$_3$, —CH$_3$, —CF3, —OCF$_3$ —CN, and —NO$_2$;

each l, m, and n are independently zero or an integer of 1 to 4;

D is selected from the group consisting of a covalent bond,

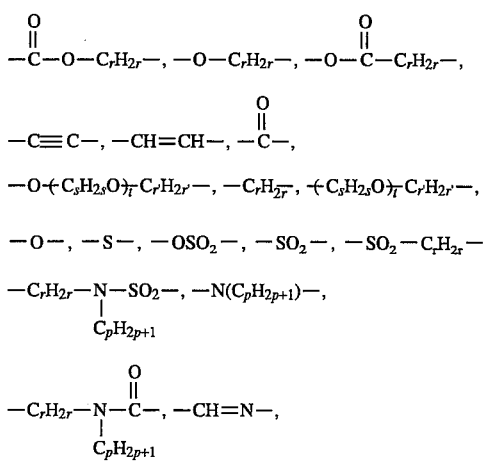

and combinations thereof, where r and r' are independently integers of 1 to about 20, s is independently an integer of 1 to about 10 for each (C$_s$H$_{2s}$O), t is an integer of 1 to about 6, and p is an integer of 0 to about 4;
R is selected from the group consisting of

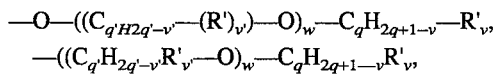
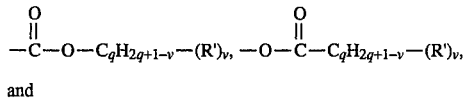

and

-continued

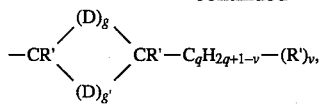

where each R' is independently selected from the group consisting of —Cl, —F, —CF$_3$, —NO$_2$, —CN, —H, —C$_q$H$_{2q+1}$,

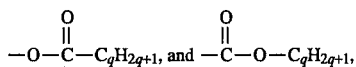

where q' is independently an integer of 1 to about 20 for each (C$_{q'}$H$_{2q'}$—O), q is an integer of 1 to about 20, w is an integer of 0 to about 10, v is an integer of 0 to about 6, each v' is independently an integer of 0 to about 6, g is an integer of 1 to about 3, g' is an integer of 1, each D is independently selected from the group set forth above, and R is linear or branched, with the proviso that R is chiral; and R$_f$ is —(C$_x$F$_{2x}$O)$_z$C$_y$F$_{2y+1}$, where x is independently an integer of 1 to about 10 for each C$_x$F$_{2x}$O, y is an integer of 1 to about 10, and z is an integer of 2 to about 10.

2. The compounds of claim 1 wherein said R$_f$ is linear, said x is independently an integer of 1 to about 6 for each C$_x$F$_{2x}$O group, said y is an integer of 1 to about 6, and said z is an integer of 2 to about 6.

3. The compounds of claim 1 wherein said compounds are represented by the formula

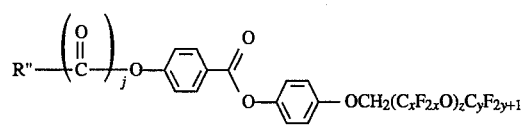

where x is independently an integer of 1 to about 6 for each C$_x$F$_{2x}$O; y is an integer of 1 to about 6; z is an integer of 2 to about 4; j is an integer of 0 or 1; and R" is selected from the group consisting of (R')$_v$—C$_q$H$_{2q+1-v}$ and

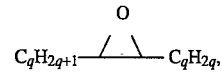

where each q is independently an integer of 2 to about 10; each R' is independently selected from the group consisting of hydrogen, fluorine, chlorine, methyl, and perfluoromethyl; v is an integer of 1 to about 4; and C$_q$H$_{2q}$ and C$_q$H$_{2q+1}$ are independently linear or branched.

4. The compounds of claim 1 wherein said compounds are represented by the formula

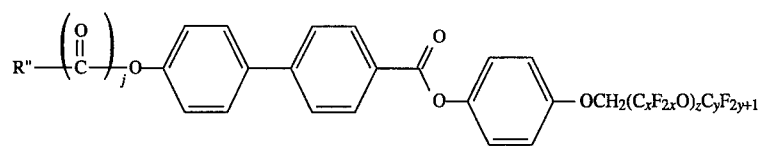

where x is independently an integer of 1 to about 6 for each C$_x$F$_{2x}$O; y is an integer of 1 to about 6; z is an integer of 2 to about 4; j is an integer of 0 or 1; and R" is selected from the group consisting of (R')$_v$—C$_q$H$_{2q+1-v}$ and

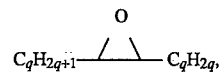

where each q is independently an integer of 2 to about 10; each R' is independently selected from the group consisting of hydrogen, fluorine, chlorine, methyl, and perfluoromethyl; v is an integer of 1 to about 4; and C$_q$H$_{2q}$ and C$_q$H$_{2q+1}$ are independently linear or branched.

5. The compounds of claim 1 wherein said compounds are represented by the formula

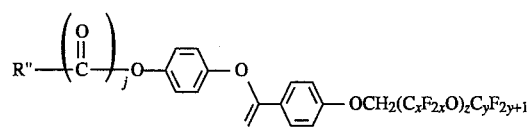

where x is independently an integer of 1 to about 6 for each C$_x$F$_{2x}$O; y is an integer of 1 to about 6; z is an integer of 2 to about 4; j is an integer of 0 or 1; and R" is selected from the group consisting of (R')$_v$—C$_q$H$_{2q+1-v}$ and

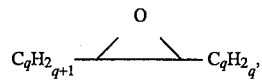

where each q is independently an integer of 2 to about 10; each R' is independently selected from the group consisting of hydrogen, fluorine, chlorine, methyl, and perfluoromethyl; v is an integer of 1 to about 4; and C$_q$H$_{2q}$ and C$_q$H$_{2q+1}$ are independently linear or branched.

6. The compounds of claim 1 wherein said compounds are represented by the formula

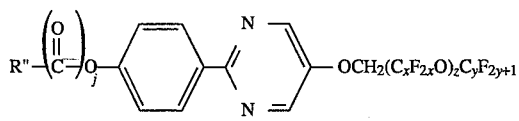

where x is independently an integer of 1 to about 6 for each $C_xF_{2x}O$; y is an integer of 1 to about 6; z is an integer of 2 to about 4; j is an integer of 0 or 1; and R" is selected from the group consisting of $(R')_v$—$C_qH_{2q+1-v}$ and

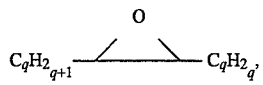

where each q is independently an integer of 2 to about 10; each R' is independently selected from the group consisting of hydrogen, fluorine, chlorine, methyl, and perfluoromethyl; v is an integer of 1 to about 4; and $C_qH_{2q+1}$ and $C_qH_{2q+1}$ are independently linear or branched.

7. The compounds of claim 1 wherein said compounds are represented by the formula

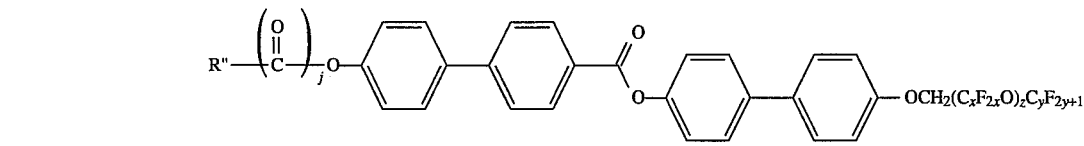

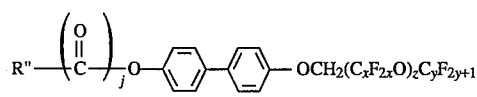

where x is independently an integer of 1 to about 6 for each $C_xF_{2x}O$; y is an integer of 1 to about 6; z is an integer of 2 to about 4; j is an integer of 0 or 1; and R" is selected from the group consisting of $(R')_v$—$C_qH_{2q+1-v}$ and

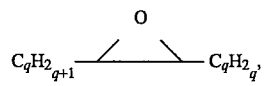

where each q is independently an integer of 2 to about 10; each R' is independently selected from the group consisting of hydrogen, fluorine. chlorine, methyl, and perfluoromethyl; v is an integer of 1 to about 4; and $C_qH_{2q}$ and $C_qH_{2q+1}$ are independently linear or branched.

8. The compounds of claim 1 wherein said compounds are represented by the formula

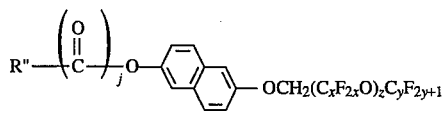

where x is independently an integer of 1 to about 6 for each $C_xF_{2x}O$; y is an integer of 1 to about 6; z is an integer of 2 to about 4; j is an integer of 0 or 1; and R" is selected from the group consisting of $(R')_v$—$C_qH_{2q+1-v}$ and

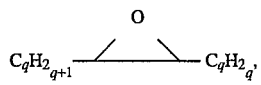

where each q is independently an integer of 2 to about 10; each R' is independently selected from the group consisting of hydrogen, fluorine, chlorine, methyl, and perfluoromethyl; v is an integer of 1 to about 4; and $C_qH_{2q}$ and $C_qH_{2q+1}$ are independently linear or branched.

9. The compounds of claim 1 wherein said compounds are represented by the formula

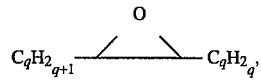

where x is independently an integer of 1 to about 6 for each $C_xF_{2x}O$; y is an integer of 1 to about 6; z is an integer of 2 to about 4; j is an integer of 0 or 1; and R" is selected from the group consisting of $(R')_v$—$C_qH_{2q+1-v}$ and where each q is independently an integer of 2 to about 10; each R' is independently selected from the group consisting of hydrogen, fluorine, chlorine, methyl, and perfluoromethyl; v is an integer of 1 to about 4; and $C_qH_{2q}$ and $C_qH_{2q+1}$ are independently linear or branched.

10. The compounds of claim 1 wherein said compounds are represented by the formula

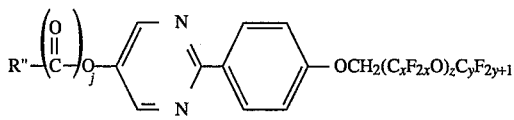

where x is independently an integer of 1 to about 6 for each $C_xF_{2x}O$; y is an integer of 1 to about 6; z is an integer of 2 to about 4; j is an integer of 0 or 1; and R" is selected from the group consisting of $(R')_v$—$C_qH_{2q+1-v}$ and

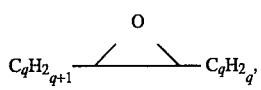

where each q is independently an integer of 2 to about 10; each R' is independently selected from the group consisting of hydrogen, fluorine, chlorine, methyl, and perfluoromethyl; v is an integer of to about 4; and $C_qH_{2q}$ and $C_qH_{2q+1}$ are independently linear or branched.

11. A process for preparing fluorine-containing, chiral liquid crystal compounds comprising the steps of (a) mixing at least one compound represented by the formula

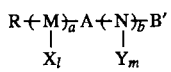

with at least one compound represented by the formula

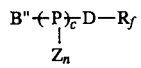

or mixing at least one compound represented by the formula

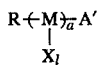

with at least one compound represented by the formula

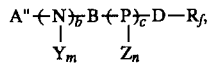

where M, N, and P are each independently selected from the group consisting of

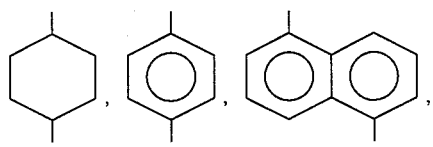

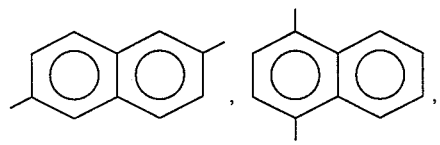

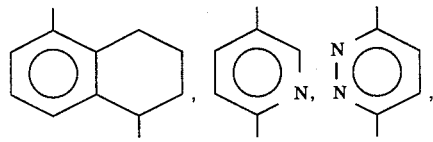

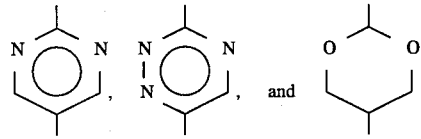

a, b, and c are each independently zero or an integer of from 1 to 3, with the proviso that the sum of a+ b+ c be at least 1;

each A and B are non-directionally and independently selected from the group consisting of a covalent bond,

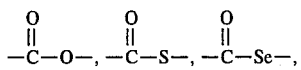

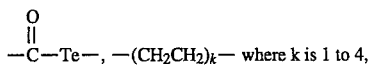

$-CH=CH-$, $-C\equiv C-$, $-CH=N-$, $-CH_2-O-$,

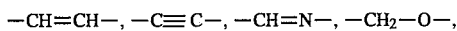

each A', A", B', and B" are independently selected from the group consisting of —OH, —COOH, —CH(CH$_2$OH)$_2$, —SH, —SeH, —the, —NH$_2$, —COCl, —CHO, —OSO$_2$R$_f'$, —OSO$_2$CH$_3$, —OSO$_2$-cyclo(C$_6$H$_4$)—CH$_3$, and —CH$_2$COOH, where R$_f'$ is a perfluoroalkyl group having from 1 to about 10 carbon atoms, and with the proviso that A' can enter into a coupling reaction with A" and that B' can enter into a coupling reaction with B";

each X, Y, and Z are independently selected from the group consisting of —H, —Cl, —F, —Br, —I, —OH, —OCH$_3$, —CH$_3$, —CF3, —OCF$_3$ —CN, and —NO$_2$;

each l, m, and n are independently zero or an integer of 1 to 4;

D is selected from the group consisting of a covalent bond,

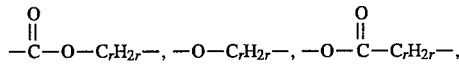

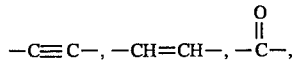

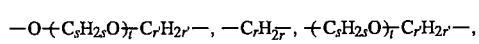

$-O-$, $-S-$, $-OSO_2-$, $-SO_2-$, $-SO_2-C_rH_{2r}-$,

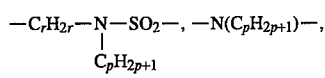

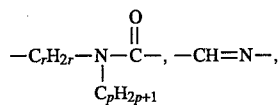

and combinations thereof, where r and r' are independently integers of 1 to about 20, s is independently an integer of 1 to about 10 for each (C$_s$H$_{2s}$O), t is an integer of 1 to about 6, and p is an integer of 0 to about 4;

R is selected from the group consisting of —O—((C$_{q'}$H$_{2q'-v}$R'$_v$)—O)$_w$—C$_q$H$_{2q+1-v}$R'$_v$, —((C$_{q'}$H$_{2q'}$—(R')$_v$)—O)$_w$—C$_q$H$_{2q+1-v}$R'$_v$,

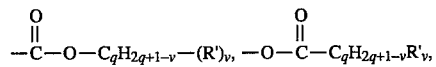

and

-continued

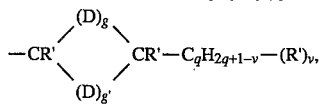

where each R' is independently selected from the group consisting of —Cl, —F, —CF$_3$, —NO$_2$, —CN, —H, —C$_q$H$_{2q+1}$,

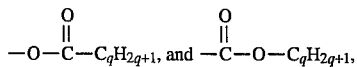

where q' is independently an integer of 1 to about 20 for each (C$_{q'}$H$_{2q'}$—O), q is an integer of 1 to about 20, w is an integer of 0 to about 10, v is an integer of 0 to about 6, each v' is independently an integer of 0 to about 6, g is an integer of 1 to about 3, g' is an integer of 1, each D is independently selected from the group set forth above other than C≡C, with the proviso that R is chiral; and R$_f$ is —(C$_x$F$_{2x}$O)$_z$C$_y$F$_{2y+1}$, where x is independently an integer of 1 to about 10 for each C$_x$F$_{2x}$O, y is an integer of 1 to about 10, and z is an integer of 2 to about 10;

and (b) allowing said A' and A" or B' and B" to react.

12. The process of claim 11 wherein said step of allowing said A' and A" or B' and B" to react is carried out in the presence of at least one coupling agent.

13. Fluorine-containing, chiral liquid crystal compounds having smectic mesophases or latent smectic mesophases, the compounds comprising (a) an aliphatic fluorocarbon terminal portion containing at least two catenary ether oxygen atoms in at least one perfluorinated segment thereof; (b) a chiral, aliphatic hydrocarbon terminal portion; and (c) a central core connecting said terminal portions.

14. The compounds of claim 13 wherein said aliphatic fluorocarbon terminal portion is represented by the formula —D(C$_x$F$_{2x}$O)$_z$C$_y$F$_{2y+1}$, where x is independently an integer of 1 to about 10 for each C$_x$F$_{2x}$O group, y is an integer of 1 to about 10, z is an integer of 2 to about 10, and D is selected from the group consisting of a covalent bond,

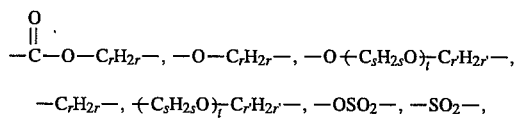

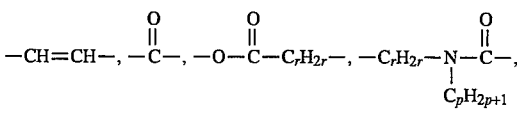

—CH=N—, —O—, —S—, —N(C$_p$H$_{2p+1}$)—, and combinations thereof, where r and r' are independently integers of 1 to about 20, s is independently an integer of 1 to about 10 for each (C$_s$H$_{2s}$O), t is an integer of 1 to about 6, and p is an integer of 0 to about 4.

15. The compounds of claim 14 wherein said x is independently an integer of 1 to about 6 for each C$_x$F$_{2x}$O group, said y is an integer of 1 to about 6, and said z is an integer of 2 to about 6.

16. A mixture of liquid crystal compounds comprising at least one fluorine-containing liquid crystal compound of claim 13.

17. The mixture of claim 16 further comprising at least one other liquid crystal compound having a fluorinated terminal portion.

18. The mixture of claim 17 wherein said other liquid crystal compound is an achiral, fluoroether-containing liquid crystal compound.

19. A liquid crystal display device containing at least one fluorine-containing liquid crystal compound of claim 13.

20. The device of claim 19 further containing at least one other liquid crystal compound having a fluorinated terminal portion.

21. The device of claim 20 wherein said other liquid crystal compound is an achiral, fluoroether-containing liquid crystal compound.

* * * * *